United States Patent
Tamarkin et al.

(10) Patent No.: US 9,320,705 B2
(45) Date of Patent: Apr. 26, 2016

(54) SENSATION MODIFYING TOPICAL COMPOSITION FOAM

(75) Inventors: Dov Tamarkin, Ness Ziona (IL); Meir Eini, Ness Ziona (IL); Doron Friedman, Karmei Yosef (IL); Ella Zlatkis, Rehovot (IL); David Schuz, Moshav Gimzu (IL); Tal Berman, Rishon Lezion (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 735 days.

(21) Appl. No.: 12/350,650

(22) Filed: Jan. 8, 2009

(65) Prior Publication Data

US 2012/0237453 A1 Sep. 20, 2012

Related U.S. Application Data

(63) Continuation of application No. 11/971,197, filed on Jan. 8, 2008, now abandoned, and a continuation-in-part of application No. 10/532,618, filed as application No. PCT/IB03/05527 on Oct. 24, 2003, said application No. 11/971,197 is a continuation-in-part of application No. 10/911,367, filed on Aug. 4, 2004, now abandoned, and a continuation-in-part of application No. 10/835,505, filed on Apr. 28, 2004, now Pat. No. 7,820,145.

(60) Provisional application No. 60/879,213, filed on Jan. 8, 2007, provisional application No. 60/429,546, filed on Nov. 29, 2002, provisional application No. 60/492,385, filed on Aug. 4, 2003, provisional application No. 60/530,015, filed on Dec. 16, 2003, provisional application No. 60/492,385, filed on Aug. 4, 2003.

(30) Foreign Application Priority Data

Oct. 25, 2002 (IL) .......................... 152486

(51) Int. Cl.
| | |
|---|---|
| A61K 9/00 | (2006.01) |
| A61K 8/04 | (2006.01) |
| A61K 8/34 | (2006.01) |
| A61K 8/42 | (2006.01) |
| A61K 8/92 | (2006.01) |
| A61K 8/97 | (2006.01) |
| A61K 9/12 | (2006.01) |
| A61Q 19/00 | (2006.01) |
| A01N 25/16 | (2006.01) |

(52) U.S. Cl.
CPC .............. *A61K 9/0014* (2013.01); *A01N 25/16* (2013.01); *A61K 8/046* (2013.01); *A61K 8/34* (2013.01); *A61K 8/345* (2013.01); *A61K 8/42* (2013.01); *A61K 8/922* (2013.01); *A61K 8/97* (2013.01); *A61K 9/122* (2013.01); *A61Q 19/00* (2013.01); *A61K 2800/24* (2013.01); *A61K 2800/242* (2013.01); *A61K 2800/244* (2013.01)

(58) Field of Classification Search
USPC .......................................................... 424/47
See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A | 1/1961 | Reed | |
| 3,004,894 A | 10/1961 | Johnson et al. | |
| 3,062,715 A | 11/1962 | Reese | |
| 3,067,784 A | 12/1962 | Gorman | |
| 3,092,255 A | 6/1963 | Hohman | |

(Continued)

FOREIGN PATENT DOCUMENTS

| | | |
|---|---|---|
| AU | 198780257 | 9/1986 |
| AU | 782515 | 12/2005 |

(Continued)

OTHER PUBLICATIONS

Prud'homme et al., Foams: theory, measurements, and applications, Marcel Dekker, Inc., 327-328, 1996.*
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.

(Continued)

*Primary Examiner* — Michael G Hartley
*Assistant Examiner* — Robert Cabral
(74) *Attorney, Agent, or Firm* — Fish & Richardson P.C.

(57) ABSTRACT

This invention relates to foamable compositions that are capable of producing a sensation or sensation modifying effect upon application on a body surface. More particularly the invention relates to foamable pharmaceutical, therapeutic and cosmetic compositions, comprising an active agent, having a sensation or sensation modifying affect on a body surface, upon application. More particularly, the invention relates to foamable compositions comprising: (a) a foamable carrier; (b) at least one sensation or sensation modifying agent, selected from the group of a cooling agent; a warming agent; a relaxing or soothing agent; stimulating or refreshing agent; or mixtures thereof and (c) a propellant at a concentration of about 3% to about 45% by weight of the total composition. The foamable carrier can be an emollient emulsion foamable vehicle, a foamable gel vehicle and can also be a substantially non aqueous foamable vehicle.

44 Claims, No Drawings

(56) References Cited

U.S. PATENT DOCUMENTS

| | | |
|---|---|---|
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brighttenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,867 A | 8/1966 | Lehmann |
| 3,263,869 A | 8/1966 | Corsette |
| 3,298,919 A | 1/1967 | Charles et al. |
| 3,301,444 A | 1/1967 | Wittke |
| 3,303,970 A | 2/1967 | Breslau et al. |
| 3,330,730 A | 7/1967 | Hernaadez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borocki |
| 3,563,098 A | 2/1971 | Weber, III |
| 3,574,821 A | 4/1971 | Pfirrmann et al. |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Sejpal et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A * | 12/1986 | Moran et al. ..................... 424/47 |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves et al. |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A * | 7/1989 | Dole et al. ..................... 424/47 |
| 4,849,117 A | 7/1989 | Bronner et al. |

(56) References Cited

U.S. PATENT DOCUMENTS

| | | |
|---|---|---|
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |

(56) References Cited

U.S. PATENT DOCUMENTS

| | | |
|---|---|---|
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,261,544 B1 | 7/2001 | Coury et al. |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |

(56) References Cited

U.S. PATENT DOCUMENTS

| | | | |
|---|---|---|---|
| 6,348,229 B1 | 2/2002 | Eini et al. |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy et al. |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 * | 5/2005 | Nakatsu et al. ............... 424/725 |
| 6,897,195 B2 | 5/2005 | Su et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,960,416 B2 | 6/2011 | Sato et al. |
| 8,114,385 B2 | 2/2012 | Tamarkin et al. |
| 8,158,109 B2 | 4/2012 | Abram et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,375 B2 | 7/2013 | Tamarkin et al. |
| 8,518,376 B2 | 8/2013 | Tamarkin et al. |
| 8,618,081 B2 | 12/2013 | Tamarkin et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 * | 12/2001 | Navarro ............... 208/401 |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |

(56) References Cited

U.S. PATENT DOCUMENTS

| | | |
|---|---|---|
| 2002/0111281 A1 | 8/2002 | Vishnupad |
| 2002/0117516 A1 | 8/2002 | Lasserre et al. |
| 2002/0122811 A1* | 9/2002 | Stein et al. .................... 424/401 |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1* | 9/2003 | Young et al. .................... 424/449 |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0014990 A1 | 1/2006 | Kuechler et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0017696 A1 | 1/2007 | Lin et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |

(56) References Cited

U.S. PATENT DOCUMENTS

| | | |
|---|---|---|
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0224143 A1* | 9/2007 | Konis et al. ............ 424/70.1 |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1* | 1/2009 | Lintner ............ A61K 8/975 424/780 |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0214628 A1* | 8/2009 | de Rijk ............ 424/450 |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0268665 A1 | 11/2011 | Tamarkin et al. |
| 2012/0064136 A1 | 3/2012 | Baker, Jr. et al. |
| 2012/0087872 A1 | 4/2012 | Tamarkin et al. |
| 2012/0128598 A1* | 5/2012 | Trumbore et al. ............ 424/45 |
| 2012/0148503 A1 | 6/2012 | Tamarkin et al. |
| 2012/0156144 A1 | 6/2012 | Tamarkin et al. |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0295022 A1 | 11/2013 | Friedman et al. |
| 2014/0050673 A1 | 2/2014 | Tamarkin et al. |
| 2014/0147504 A1 | 5/2014 | Salman et al. |
| 2014/0193502 A1 | 7/2014 | Tamarkin et al. |
| 2014/0228355 A1 | 8/2014 | Kortagere et al. |

FOREIGN PATENT DOCUMENTS

| | | |
|---|---|---|
| AU | 2010219295 | 9/2012 |
| CA | 2114537 | 2/1993 |
| CA | 2154438 * | 1/1996 |
| CA | 2422244 | 9/2003 |
| CA | 2502986 | 8/2011 |
| CA | 2534372 | 1/2012 |
| CA | 2536482 | 7/2012 |
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0156507 A1 | 10/1985 |
| EP | 0 186 453 | 7/1986 |
| EP | 0186453 | 7/1986 |
| EP | 0 211 550 | 2/1987 |
| EP | 211550 | 2/1987 |
| EP | 0 213 827 | 3/1987 |
| EP | 0 214 865 | 3/1987 |
| EP | 0214865 A2 | 3/1987 |
| EP | 0216856 | 4/1987 |
| EP | 0270316 | 6/1988 |
| EP | 0 297 436 | 1/1989 |
| EP | 297436 | 1/1989 |
| EP | 326196 | 8/1989 |
| EP | 336812 | 10/1989 |
| EP | 0391124 B1 | 10/1990 |
| EP | 0 404 376 | 12/1990 |
| EP | 0404376 | 12/1990 |
| EP | 0 414 920 | 3/1991 |
| EP | 414920 | 3/1991 |
| EP | 0 484 530 | 5/1992 |
| EP | 0484530 A1 | 5/1992 |
| EP | 485299 | 5/1992 |
| EP | 0 488 089 | 6/1992 |
| EP | 0488089 A1 | 6/1992 |

(56) References Cited

FOREIGN PATENT DOCUMENTS

| | | |
|---|---|---|
| EP | 504301 | 9/1992 |
| EP | 0506197 B2 | 9/1992 |
| EP | 0 528 190 | 2/1993 |
| EP | 0 535 327 | 4/1993 |
| EP | 0535327 | 4/1993 |
| EP | 0 552 612 | 7/1993 |
| EP | 0 569 773 | 11/1993 |
| EP | 0569773 A2 | 11/1993 |
| EP | 0598412 | 11/1993 |
| EP | 0 598 412 | 5/1994 |
| EP | 0 662 431 | 7/1995 |
| EP | 0 676 198 | 10/1995 |
| EP | 0676198 | 10/1995 |
| EP | 0 738 516 | 10/1996 |
| EP | 0738516 | 10/1996 |
| EP | 0 757 959 | 2/1997 |
| EP | 0 824 911 | 2/1998 |
| EP | 0824911 | 2/1998 |
| EP | 829259 | 3/1998 |
| EP | 928608 | 7/1999 |
| EP | 0 979 654 | 2/2000 |
| EP | 0979654 A1 | 2/2000 |
| EP | 0 993 827 | 4/2000 |
| EP | 0993827 A1 | 4/2000 |
| EP | 1025836 A1 | 8/2000 |
| EP | 1 055 425 | 11/2000 |
| EP | 1055425 A2 | 11/2000 |
| EP | 1 215 258 | 6/2002 |
| EP | 1215258 | 6/2002 |
| EP | 1 287 813 | 3/2003 |
| EP | 1287813 | 3/2003 |
| EP | 1308169 | 5/2003 |
| EP | 1 375 386 | 1/2004 |
| EP | 1397118 | 3/2004 |
| EP | 1 428 521 | 6/2004 |
| EP | 1428521 | 6/2004 |
| EP | 1 438 946 | 7/2004 |
| EP | 1438946 | 7/2004 |
| EP | 1 189 579 | 9/2004 |
| EP | 1189579 | 9/2004 |
| EP | 1 475 381 | 11/2004 |
| EP | 1475381 | 11/2004 |
| EP | 1483001 | 12/2004 |
| EP | 1 500 385 | 1/2005 |
| EP | 1500385 | 1/2005 |
| EP | 1 537 916 | 6/2005 |
| EP | 1600185 | 11/2005 |
| EP | 1 734 927 | 12/2006 |
| EP | 1 758 547 | 3/2007 |
| EP | 1758547 | 3/2007 |
| EP | 1 584 324 | 11/2007 |
| EP | 1584324 | 11/2007 |
| EP | 1889609 | 2/2008 |
| EP | 2422768 | 2/2012 |
| EP | 2494959 | 9/2012 |
| FR | 2 456 522 | 12/1980 |
| FR | 2 591 331 | 6/1987 |
| FR | 2 640 942 | 6/1990 |
| FR | 2736824 | 1/1997 |
| FR | 2 774 595 | 8/1999 |
| FR | 2774595 A | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2840903 | 12/2003 |
| FR | 2 843 373 | 2/2004 |
| FR | 2 845 672 | 4/2004 |
| FR | 2 848 998 | 6/2004 |
| FR | 2860976 | 4/2005 |
| FR | 2 915 891 | 11/2008 |
| FR | 2915891 | 11/2008 |
| GB | 808 104 | 1/1959 |
| GB | 808 105 | 1/1959 |
| GB | 808104 | 1/1959 |
| GB | 808105 | 1/1959 |
| GB | 922 930 | 4/1963 |
| GB | 922930 | 4/1963 |
| GB | 933 486 | 8/1963 |
| GB | 933486 | 8/1963 |
| GB | 998 490 | 7/1965 |
| GB | 1 026 831 | 4/1966 |
| GB | 1026831 | 4/1966 |
| GB | 1033299 | 6/1966 |
| GB | 1081949 A | 9/1967 |
| GB | 1 121 358 | 7/1968 |
| GB | 1121358 | 7/1968 |
| GB | 1 162 684 | 8/1969 |
| GB | 1 170 152 | 11/1969 |
| GB | 1170152 | 11/1969 |
| GB | 1 201 918 | 8/1970 |
| GB | 1347950 | 2/1974 |
| GB | 1 351 761 | 5/1974 |
| GB | 1 351 762 | 5/1974 |
| GB | 1 353 381 | 5/1974 |
| GB | 1376649 | 12/1974 |
| GB | 1 397 285 | 6/1975 |
| GB | 1397285 | 6/1975 |
| GB | 1408036 | 10/1975 |
| GB | 1 457 671 | 12/1976 |
| GB | 1489672 A | 10/1977 |
| GB | 2004746 A | 4/1979 |
| GB | 1561423 | 2/1980 |
| GB | 2 114 580 | 8/1983 |
| GB | 2114580 | 8/1983 |
| GB | 2153686 | 8/1985 |
| GB | 2172298 | 9/1986 |
| GB | 2 206 099 | 12/1988 |
| GB | 2 166 651 | 5/1996 |
| GB | 2166651 | 5/1996 |
| GB | 2 337 461 | 11/1999 |
| GB | 2337461 | 11/1999 |
| GB | 2 367 809 | 4/2002 |
| GB | 2 406 330 | 3/2005 |
| GB | 2406791 | 4/2005 |
| GB | 2 474 930 | 7/2012 |
| IL | 49491 | 9/1979 |
| IL | 152 486 | 5/2003 |
| IL | 0152486 | 5/2003 |
| JP | S48-92282 | 11/1973 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 01100111 | 4/1989 |
| JP | 1100111 | 4/1989 |
| JP | 1156906 | 6/1989 |
| JP | 01156906 | 6/1989 |
| JP | 2184614 | 7/1990 |
| JP | 02184614 A | 7/1990 |
| JP | 2255890 | 10/1990 |
| JP | 04282311 | 10/1992 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |

(56) References Cited

FOREIGN PATENT DOCUMENTS

| | | |
|---|---|---|
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000017174 A | 1/2000 |
| JP | 2000/080017 | 3/2000 |
| JP | 2000080017 | 3/2000 |
| JP | 2000/128734 | 5/2000 |
| JP | 2000128734 | 5/2000 |
| JP | 2000/191429 | 7/2000 |
| JP | 2000191429 | 7/2000 |
| JP | 2000239140 | 9/2000 |
| JP | 2000/351726 | 12/2000 |
| JP | 2000351726 | 12/2000 |
| JP | 2000354623 | 12/2000 |
| JP | 2001/019606 | 1/2001 |
| JP | 2001002526 | 1/2001 |
| JP | 2001019606 | 1/2001 |
| JP | 2001/072963 | 3/2001 |
| JP | 2001072963 | 3/2001 |
| JP | 2002/012513 | 1/2002 |
| JP | 2002012513 | 1/2002 |
| JP | 2002047136 | 2/2002 |
| JP | 2002/524490 | 8/2002 |
| JP | 2002302419 | 10/2002 |
| JP | 2003/012511 | 1/2003 |
| JP | 2003/055146 | 2/2003 |
| JP | 2003055146 | 2/2003 |
| JP | 2004/047136 | 2/2004 |
| JP | 2004047136 A | 2/2004 |
| JP | 2004250435 | 9/2004 |
| JP | 2004/348277 | 12/2004 |
| JP | 2005314323 | 11/2005 |
| JP | 2005/350378 | 12/2005 |
| JP | 2005350378 | 12/2005 |
| JP | 2006/008574 | 1/2006 |
| JP | 2006008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| JP | 2007131539 | 5/2007 |
| KR | 143232 | 7/1998 |
| KR | 2001003063 | 1/2001 |
| NZ | 520014 | 5/2005 |
| NZ | 540166 | 6/2007 |
| RU | 2277501 | 6/2006 |
| UA | 66796 | 6/2004 |
| WO | WO-8201821 A1 | 6/1982 |
| WO | WO-86/05389 | 9/1986 |
| WO | WO 86/05389 | 9/1986 |
| WO | WO-88/01863 | 3/1988 |
| WO | WO 88/01863 | 3/1988 |
| WO | WO-8801502 | 3/1988 |
| WO | WO-88/08316 | 11/1988 |
| WO | WO 89/06537 | 7/1989 |
| WO | WO-89/06537 | 7/1989 |
| WO | WO 90/05774 | 5/1990 |
| WO | WO-90/05774 | 5/1990 |
| WO | WO 91/11991 | 8/1991 |
| WO | WO-91/11991 | 8/1991 |
| WO | WO 92/00077 | 1/1992 |
| WO | WO-92/00077 | 1/1992 |
| WO | 92/05763 | 4/1992 |
| WO | WO-9205142 A1 | 4/1992 |
| WO | WO 92/11839 | 7/1992 |
| WO | WO-92/11839 | 7/1992 |
| WO | WO 92/13602 | 8/1992 |
| WO | WO-9325189 A1 | 12/1993 |
| WO | WO-9406440 A1 | 3/1994 |
| WO | WO 96/03115 | 2/1996 |
| WO | WO-96/03115 | 2/1996 |
| WO | WO-96/19921 | 7/1996 |
| WO | WO 96/19921 | 7/1996 |
| WO | WO-9624325 A1 | 8/1996 |
| WO | 96/26711 | 9/1996 |
| WO | WO 96/27376 | 9/1996 |
| WO | WO-96/27376 | 9/1996 |
| WO | WO-96/39119 | 12/1996 |
| WO | WO 96/39119 | 12/1996 |
| WO | WO-9703638 | 2/1997 |
| WO | WO-97/39745 | 10/1997 |
| WO | WO 97/39745 | 10/1997 |
| WO | WO-9817282 A1 | 4/1998 |
| WO | WO 98/18472 | 5/1998 |
| WO | WO-98/18472 | 5/1998 |
| WO | WO-98/19654 | 5/1998 |
| WO | WO 98/19654 | 5/1998 |
| WO | WO-98/21955 | 5/1998 |
| WO | WO 98/21955 | 5/1998 |
| WO | WO 98/23291 | 6/1998 |
| WO | WO-98/23291 | 6/1998 |
| WO | WO 98/31339 | 7/1998 |
| WO | WO-98/36733 | 8/1998 |
| WO | WO 98/36733 | 8/1998 |
| WO | 98/52536 | 11/1998 |
| WO | WO-99/08649 | 2/1999 |
| WO | WO 99/08649 | 2/1999 |
| WO | WO 99/20250 | 4/1999 |
| WO | WO-99/20250 | 4/1999 |
| WO | WO 99/37282 | 7/1999 |
| WO | WO-99/37282 | 7/1999 |
| WO | WO-9953923 A1 | 10/1999 |
| WO | WO 00/09082 | 2/2000 |
| WO | WO-00/09082 | 2/2000 |
| WO | WO 00/15193 | 3/2000 |
| WO | WO-00/15193 | 3/2000 |
| WO | WO 00/62776 | 4/2000 |
| WO | WO-0023051 | 4/2000 |
| WO | WO-0033825 | 6/2000 |
| WO | WO-0038731 | 7/2000 |
| WO | WO-00/61076 | 10/2000 |
| WO | WO 00/61076 | 10/2000 |
| WO | WO 00/72805 | 12/2000 |
| WO | WO-00/76461 | 12/2000 |
| WO | WO 00/76461 | 12/2000 |
| WO | 01/05366 | 1/2001 |
| WO | WO 01/08681 | 2/2001 |
| WO | WO-01/08681 | 2/2001 |
| WO | WO-0110961 A1 | 2/2001 |
| WO | 01/53198 | 7/2001 |
| WO | 01/54212 | 7/2001 |
| WO | WO-01/54679 | 8/2001 |
| WO | WO 01/54679 | 8/2001 |
| WO | WO-0162209 A2 | 8/2001 |
| WO | WO 01/70242 | 9/2001 |
| WO | WO-01/70242 A2 | 9/2001 |
| WO | 01/82890 | 11/2001 |
| WO | WO 01/82880 | 11/2001 |
| WO | WO-01/82880 | 11/2001 |
| WO | WO-0185102 A2 | 11/2001 |
| WO | WO-0185128 | 11/2001 |
| WO | WO-0195728 A1 | 12/2001 |
| WO | WO-02/00820 | 1/2002 |
| WO | WO 02/00820 | 1/2002 |
| WO | WO 0207685 A2 * | 1/2002 |
| WO | WO-0215860 | 2/2002 |
| WO | WO-0215873 | 2/2002 |
| WO | WO 02/24161 | 3/2002 |
| WO | WO-02/28435 | 4/2002 |
| WO | WO 02/28435 | 4/2002 |
| WO | WO 02/41847 | 5/2002 |
| WO | WO-02/41847 A1 | 5/2002 |
| WO | WO-02/43490 | 6/2002 |
| WO | WO 02/43490 | 6/2002 |
| WO | WO 02/062324 | 8/2002 |
| WO | WO-02/062324 | 8/2002 |
| WO | WO-02078667 A1 | 10/2002 |
| WO | WO-02087519 | 11/2002 |
| WO | WO 03/005985 | 1/2003 |
| WO | WO-03000223 A1 | 1/2003 |
| WO | WO-03002082 | 1/2003 |
| WO | 03/013984 | 2/2003 |

(56) References Cited

FOREIGN PATENT DOCUMENTS

| | | |
|---|---|---|
| WO | WO 03/051294 | 6/2003 |
| WO | WO-03/051294 | 6/2003 |
| WO | WO 03/053292 | 7/2003 |
| WO | WO-03/053292 | 7/2003 |
| WO | WO-03/055445 | 7/2003 |
| WO | WO 03/055445 | 7/2003 |
| WO | WO-03055454 | 7/2003 |
| WO | 03/070301 | 8/2003 |
| WO | 03/071995 | 9/2003 |
| WO | WO-03/075851 | 9/2003 |
| WO | WO 03/075851 | 9/2003 |
| WO | 03/097002 | 11/2003 |
| WO | WO-03/092641 | 11/2003 |
| WO | WO 03/092641 | 11/2003 |
| WO | WO 03/094873 | 11/2003 |
| WO | WO-2004017962 | 3/2004 |
| WO | WO-2004/037225 | 5/2004 |
| WO | WO 2004/037225 | 5/2004 |
| WO | WO-2004037197 | 5/2004 |
| WO | 2004/003284 | 8/2004 |
| WO | WO 2004/064833 | 8/2004 |
| WO | WO-2004/064833 | 8/2004 |
| WO | WO 2004/071479 | 8/2004 |
| WO | WO-2004/071479 A1 | 8/2004 |
| WO | WO-2004064769 | 8/2004 |
| WO | WO 2004/078896 | 9/2004 |
| WO | WO-2004/078896 | 9/2004 |
| WO | WO-2004078158 | 9/2004 |
| WO | WO-2004093895 | 11/2004 |
| WO | WO-2004/112780 | 12/2004 |
| WO | WO 2004/112780 | 12/2004 |
| WO | WO 2005/011567 | 2/2005 |
| WO | WO-2005/011567 A2 | 2/2005 |
| WO | WO 2005/018530 | 3/2005 |
| WO | WO-2005/018530 | 3/2005 |
| WO | WO 2005/032522 | 4/2005 |
| WO | WO-2005/032522 | 4/2005 |
| WO | WO 2005/044219 | 5/2005 |
| WO | WO-2005/044219 | 5/2005 |
| WO | WO-2005/065652 | 7/2005 |
| WO | WO 2005/065652 | 7/2005 |
| WO | WO-2005063224 | 7/2005 |
| WO | WO-2005/076697 | 8/2005 |
| WO | WO 2005/076697 | 8/2005 |
| WO | WO 2005/097068 | 10/2005 |
| WO | WO-2005/097068 | 10/2005 |
| WO | WO 2005/102539 | 11/2005 |
| WO | WO-2005/102539 A | 11/2005 |
| WO | WO-2005102282 A1 | 11/2005 |
| WO | WO-2005/117813 | 12/2005 |
| WO | WO 2005/117813 | 12/2005 |
| WO | WO 2006/003481 | 1/2006 |
| WO | WO-2006/003481 A2 | 1/2006 |
| WO | 2006/020682 | 2/2006 |
| WO | WO-2006/010589 | 2/2006 |
| WO | WO 2006/010589 | 2/2006 |
| WO | WO-2006011046 | 2/2006 |
| WO | WO 2006/031271 | 3/2006 |
| WO | WO-2006/031271 | 3/2006 |
| WO | WO-2006028339 A1 | 3/2006 |
| WO | WO-2006045170 A2 | 5/2006 |
| WO | WO 2006/091229 | 8/2006 |
| WO | WO-2006/091229 | 8/2006 |
| WO | WO-2006079632 A1 | 8/2006 |
| WO | WO-2006081327 | 8/2006 |
| WO | WO 2006/100485 | 9/2006 |
| WO | WO-2006/100485 | 9/2006 |
| WO | WO-2006120682 | 11/2006 |
| WO | WO-2006120682 A2 | 11/2006 |
| WO | WO-2006121610 A2 | 11/2006 |
| WO | WO-2006122158 | 11/2006 |
| WO | WO-2006/129161 | 12/2006 |
| WO | WO 2006/129161 | 12/2006 |
| WO | WO 2006/131784 | 12/2006 |
| WO | WO-2006/131784 | 12/2006 |
| WO | WO 2007/007208 | 1/2007 |
| WO | WO-2007/007208 | 1/2007 |
| WO | WO 2007/010494 | 1/2007 |
| WO | WO-2007/012977 | 2/2007 |
| WO | WO 2007/012977 | 2/2007 |
| WO | WO-2007/023396 | 3/2007 |
| WO | WO 2007/023396 | 3/2007 |
| WO | WO 2007/031621 | 3/2007 |
| WO | WO-2007/031621 A2 | 3/2007 |
| WO | WO-2007/039825 | 4/2007 |
| WO | WO 2007/039825 | 4/2007 |
| WO | WO 2007/050543 | 5/2007 |
| WO | WO-2007/050543 | 5/2007 |
| WO | WO 2007/054818 | 5/2007 |
| WO | WO-2007/054818 | 5/2007 |
| WO | WO 2007/072216 | 6/2007 |
| WO | WO-2007/072216 | 6/2007 |
| WO | WO 2007/082698 | 7/2007 |
| WO | WO 2007/085899 * | 8/2007 |
| WO | WO-2007/085899 | 8/2007 |
| WO | WO 2007/085902 | 8/2007 |
| WO | WO-2007/085902 | 8/2007 |
| WO | WO-2007/099396 | 9/2007 |
| WO | WO 2007/099396 | 9/2007 |
| WO | WO-2007111962 A2 | 10/2007 |
| WO | WO-2008/008397 | 1/2008 |
| WO | WO 2008/008397 | 1/2008 |
| WO | WO-2008010963 | 1/2008 |
| WO | 2008/041045 | 4/2008 |
| WO | WO-2008/038147 | 4/2008 |
| WO | WO 2008/038147 | 4/2008 |
| WO | WO 2008/075207 | 6/2008 |
| WO | WO-2008/075207 | 6/2008 |
| WO | WO-2008/087148 | 7/2008 |
| WO | WO 2008/087148 | 7/2008 |
| WO | WO 2008/110872 | 9/2008 |
| WO | WO-2008/110872 A2 | 9/2008 |
| WO | 2008/152444 | 12/2008 |
| WO | WO 2009/007785 | 1/2009 |
| WO | WO-2009/007785 A2 | 1/2009 |
| WO | WO 2009/069006 | 6/2009 |
| WO | WO-2009/069006 A2 | 6/2009 |
| WO | WO 2009/072007 | 6/2009 |
| WO | WO-2009/072007 A2 | 6/2009 |
| WO | 2009090558 | 7/2009 |
| WO | WO 2009/087578 | 7/2009 |
| WO | WO-2009/087578 A2 | 7/2009 |
| WO | WO 2009/090495 | 7/2009 |
| WO | WO-2009/090495 A2 | 7/2009 |
| WO | WO 2009/090558 | 7/2009 |
| WO | WO-2009/090558 A2 | 7/2009 |
| WO | WO 2009/098595 | 8/2009 |
| WO | WO-2009/098595 A2 | 8/2009 |
| WO | WO-2011039637 | 4/2011 |
| WO | WO-2011039638 | 4/2011 |
| WO | WO 2011/138678 | 11/2011 |
| WO | WO 2013/136192 | 9/2013 |

OTHER PUBLICATIONS

"Minocycline" accessed on Ocotober 21, 2011 at en.wikipedia.org/wiki/Minocycline, 7 pages.

'Niram Chemicals' [online] Niram Chemicals, [retrieved on Jul. 17, 2012]. Retrieved from the Internet: <URL: http://www.indiamart.com/niramchemicals/chemicals.html>, 7 pages.

Barry and Badal, "Stability of minocycline, doxycycline, and tetracycline stored in agar plates and microdilution trays," *Current Microbiology*, 1978, 1:33-36.

Hargreaves, "Chemical Formulation, An Overview of Surfactant-Based Preparations Used in Everyday Life", *The Royal Society of Chemistry*, pp. 114-115 (2003).

Hormones. Http://www.greenwillowtree.com/Page.bok?file=libido.html. Jan. 2001.

Joseph, "Understanding foams & foaming," University of Minnesota (1997), at http://www.aem.umn.edu/people/faculty/joseph/archive/docs/understandingfoams.pdf, pp. 1-8.

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

(56) References Cited

OTHER PUBLICATIONS

Martindale. 33 ed. London, Bath Press, 2002. pp. 1073 and 1473.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
Oil. Dictionary of Chemistry. Editor: DWA Sharp. Copyright 1990.
Padhi et al., "Phospho-olicines as positive-electrode materials for rechargeable lithium batteries," *J. Electrochemical Soc.*, 1997, 144(4): 1188-1194.
Ravet et al., "Electroactivity of natural and synthetic triphylite," *J. of Power Sources*, 2001, 97-98: 503-507.
Shrestha et al., "Forming properties of monoglycerol fatty acid esters in nonpolar oil systems," *Langmuir*, 2006, 22: 8337-8345.
Surfactant. Chemistry Glossary. Http://chemistry.about.com/od/chemistryglossary/g/surfactant.htm, 2012, 1 page.
Third Party Submission for U.S. Appl. No. 12/014,088, Feb. 4, 2009, 4 pages.
Yamada and Chung, "Crystal Chemistry of the Olivine-Type $Li(Mn_yFe_{1-y})PO_4$ and $(Mn_yFe_{1-y})PO_4$ as Possible 4 V Cathode Materials for Lithium Batteries," *J. Electrochemical Soc.*, 2001, 148(8): A960-967.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol.*, 1999, 79:418-21.
Garti et al., "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris*," *J. Chem. Ecol.*, 11: 1297-1306, 1985.
Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.
Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci*, USA, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol.*, 1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3): 190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.

(56) References Cited

OTHER PUBLICATIONS

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

International Preliminary Report on Patentability from PCT/IB2009/005005, dated Jul. 13, 2010; International Search Report, dated Apr. 27, 2010, 16 pages.

"Arquad HTL8-MS," AkzoNobel Functional Applications, retrieved on Mar. 18, 2013, Retrieved from the Internet: <URL: http://sc.akzonobel.com/en/fa/Pages/product-detail.aspx?prodID=8764>, 1 page.

"Can tuberous sclerosis be prevented?," Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.

"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.

"Dacarbazine," *Chemical Book*, 2010, retrieved on Oct. 18, 2013, <URL: http://www.chemicalbook.com/ChemicalProductProperty_EN_CB7710656.htm>, 2 pages.

"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.

"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.

"Gas Gangrene," Merch Manual Home Edition, 2008, retrieved on Jan. 16, 2013, <http://www.merckmanuals.com/home/infections/bacterial_infections/gas_gangrene.html?qt=gas gangrene&alt=sh>1 page.

"Human Immunodeficiency Virus Infection," Merch Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh>, 11 pages.

"Minocycline (DB01017)," DrugBank, Feb. 8, 2013, retrieved on Aug. 15, 2013, <http://www.drugbank.ca/drugs/DB01017>, 10 pages.

"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.

"Product Data Sheet for Meclocycline," *bioaustralis fine chemicals*, Jun. 28, 2013, 1 page.

"Shear," Vocabulary.com, retrieved on Aug. 23, 2013, <URL: https://www.vocabulary.com/dictionary/shear>, 3 pages.

"Sheer," Vocabulary.com, retrieved on Aug. 23, 2013, <URL: https://www.vocabulary.com/dictionary/sheer>, 3 pages.

"View of NCT01171326 on Dec. 7, 2010," ClinicalTrials.gov_archive, Dec. 7, 2010, retrieved on Sep. 9, 2013, <http://clinicaltrials.gov/archive/NCT01171326/2010_12_07>, 4 pages.

"View of NCT01362010 on Jun. 9, 2011," ClinicalTrials.gov_archive, Jun. 9, 2011, retrieved on Sep. 9, 2013, < http://clinicaltrials.gov/archive/NCT01362010/2011_06_09>, 3 pages.

"What is TSC?," *Tuberous Sclerosis Alliance*, Jan. 1, 2005, retrieved on Feb. 6, 2014, <URL: http://www.tsalliance.org.pages.aspx?content=2>, 3 pages.

'Surfactant' [online]. Wikipedia, 2010, [retrieved on Oct. 24, 2010]. Retrieved from the Internet: <URL: http://en.wikipedia.org/wiki/Surfactant>, 7 pages.

Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.

Alcohol SDA 40B.http://www.pharmco-prod.com/pages/MSDS/SDA.sub.--40B.sub.--200.pdf Accessed Dec. 9, 2008, 2 pages.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Blaney and Cook, "Topical use of tetracycline in the treatment of acne," Arch Dermatol, Jul. 1976, 112:971-973.

Brenes, et al., "Stability of Copigmented Anthocyanins and Asorbics Acid in a Grape Juice Model System", J. Agric Food Chem, 53(1):49-56 (2005)—Abstrace, 1 page.

Carbowax 1000MSDS; http://www.sciencelab.com/xMSDS-Polyethylene.sub.--glycol.sub.--1000-9926-622. Accessed Dec. 13, 2008, 6 pages.

Cetearyl Alcohol, Natural Wellbeing, Copyrigh 2001-2012, retrieved on Apr. 10, 2014, http://www.naturalwellbeing.com/learning-center/Cetearyl_Alcohol, 3 pages.

Cunha, "Minocycline versus Doxycycline in the treatment of Lyme Neuroborreliosis," *Clin. Infect. Diseases*, 2000, 30: 237-238.

Denatonium Benzoate http://www.newdruginfo.com/pharmaceopeia/usp28/v28230/usp28nf23s0.sub.--m- 22790.htm Accessed Dec. 9, 2008, 2 pages.

Durian et al., "Scaling behavior in shaving cream," The Americal Physical Society, Dec. 1991, 44(12):R7902-7905.

Emulsifiers with HLB values. http://www.theherbarie.com/files/resources-center/formulating/Emulsifiers- .sub.--HLB.sub.--Values.pdf accessed Aug. 5, 2009 (3 pps).

Encyclopedia of Pharmaceutical Technology, Second Edition, vol. 3, Copyright 2002, 4 pages.

Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gill, A.M, et al., "Adverse Drug Reactions in a Paediatric Intensive Care Unit," Acta Paediatr 84:438-441, 1995.

Google search strategy for minocycline solubility, retrieved on Aug. 15, 2013, <http://www.googl.com/search?rls=com.microsoft%3Aen-us%3AIE-SearchBox&q-melocycline+solubility>, 1 page.

Hall, Karla, "Diaper Area Hemangiomas: A Unique Set of Concerns," http://members.tripod.com/.about.Michelle.sub.--G/diaper.html, Dec. 1, 2008, 8 pages.

Harry, "Skin Penetration," *The British Journal of Dermatology and Syphillis*, 1941, 53:65-82.

http://ibabydoc.com/online/diseaseeczema.asp., Atopic Dermatitis, Copyright 2000, 6 pages.

http://web .archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hydroxyethylcellulose. Http: //terpconnect.umd.edu/-choi/MSDS/Sigma-Aldrich/HYDROXYETHYL%2OCELLULOSE, 5 pages, Jan. 14, 2004.

Kathon.TM. CG (product information sheet by Rohm and Haas, Jun. 2006).

Kinnunen, "Skin reactions to hexylene glycol," Contact Dermatitis Sep. 1989; 21(3): 154-8.

(56) References Cited

OTHER PUBLICATIONS

Koerber, S., "Humectants and Water Activity," Water Activity News, 2000, ISSN No. 1083-3943.
Lee et al., "Historical review of melanoma treatment and outcomes," Clinics in Dermatology, 2013, 31: 141-147.
Licking Vaginal Dryness without a Prescription. Accessed http://www.estronaut.com/a/vag.sub.--dryness.htm on Dec. 14, 2008, 3 pages.
Livingstone and Hubel, "Segregation of form, color, movement, and depth: Anatomy, physiology, and perception," Science, May 1988, 240:740-749.
MMP Inc. International Development and Manufacturing, "Formulating specialities," http://mmpinc.com, 3 pages. Feb. 2, 2010.
*Molins PLC v. Textron Inc.*, 48 F.3d 1172, 33 USPQ2d 1823 (Fed. Cir. 1995), 19 pages.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," Current Drug Delivery, 2009, 6:83-92.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Pendergrass, "The shape and dimension of the human vagina as seen in three-dimensional vinyl polysiloxane casts," Gynecol Obstet. Invest. 1996:42(3):178-82.
Prud'homme et al., Foams: theory, measurements and applications, Marcel Dekker, Inc., 1996, 327-328.
Purdy et al., "Transfusion-transmitted malaria: unpreventable by current donor exclusion guidelines?" Transfusion, Mar. 2004, 44:464.
Reregistration Eligibility Decision for Pyrethrins, EPA, Jun. 7, 2006, 108 pages.
Schmolka, "A review of block polymer surfactants," *Journal of the American Oil Chemists Society*, Mar. 1977, 54: 110-116.
Schott, "Rheology," *Remington's Pharmaceutical Sciences*, 17th Edition, 1985, 330-345.
Sciarra, "Aerosol Technology," Kirk-Othmer Encyclopedia of Chemical Technology, Jul. 2012, 20 pages.
Scott as Published in Pharmaceutical Dosage Forms; Disperse Systems, vol. 3, Copyright 1998, 120 pages.
Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.
Sehgal, "Ciclopirox: a new topical pyrodonium antimycotic agent: A double-blind study in superficial dermatomycoses," *British Journal of Dermatology*, 1976, 95:83-88.
Sigma Aldrich, "HLB-Numbers in Lithography Nanopatterning," http://www.sigmaaldrich.com/materials-science/micro-and-nanoelectronics/l-ithography-nanopatterning/hlb-numbers.html, accessed: Feb. 2, 2009, pp. 1-3.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.
Softemul-165: Product Data Sheet, Mohini Organics PVT LTD, retrieved Apr. 10, 2014, http://www.mohiniorganics.com/Softemul165.html#, 1 page.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).
*Sun Pharmaceutical Industried Ltd.* v. *Eli Lilly and Co.*, 611 F.3d 1381, 95 USPQ2d 1797 (Fed. Cir. 2010),7 pages.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tavss et al., "Anionic detergent-induced skin irritation and anionic detergent-induced pH rise of bovine serum albumin," J. Soc. Cosmet. Chem., Jul./Aug. 1988, 39:267-272.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Wormser, Early topical treatment with providone-iodine ointment reduces, and sometimes prevents, skin damage following heat stimulus, Letter to the Editor, Burns 24, pp. 383, 1998.
Gels, UNC, The Pharmaceutics and Compounding Laboratory, retrieved on Aug. 25, 2014, http://pharmlabs.unc.edu/labs/gels/agents/htm, 4 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Omega-9 Fatty Acids (Oleic Acid), Orthomolecular.org, Dec. 2004, retrieved on Aug. 15, 2014, http://orthomolecular.org/nutrients/omega9.html. 1 page.
Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008, 8 pages.
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0_m22790.htm Accessed Dec. 9, 2008, 2 pages.
Edirisinghe, et al., "Effect of fatty acids on endothelium-dependent relaxation in the rabbit aorta", Clin Sci (Lond). Aug. 2006; 111(2): 145-51.
Emulsifiers with HLB values. http://www.theherbarie.com/files/resources-center/formulating/Emulsifiers_HLB_Values.pdf accessed Aug. 5, 2009 (3 pps).
Encyclopedia of Pharmaceutical Technology, Second Edition, vol. 3, Copyright 2002.
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.

(56) References Cited

OTHER PUBLICATIONS

Flick, Cosmetic and Toiletry Formulations, vol. 5, 2nd Edition, Copyright 1996.
Fontana, Anthony, J., "Water Activity: Why It Is Important for Food Safety," International Conference on Food Safety, Nov. 16-18, 1998, 9 pages.
Galligan, John et al., "Adhesive Polyurethane Liners for Anterior Restorations," J. Dent. Res., Jul.-Aug. 1968, pp. 629-632.
Gill, A.M, et al., "Adverse Drug Reactions in a Paediatric Intensitve Care Unit," Acta Paediatr 84:438-441, 1995.
Glaser, et al., Hyperhidrosis: A Comprehensive and Practical Approach to Patient Management, Expert Rev. Dermatol. 1(6), 773-775 (2006).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemanglomas: A Unique Set of Concerns," http://members.tripod.com/~Michelle_G/diaper.html, Dec. 1, 2008, 8 pages.
Hashim, et al. "Tinea versicolor and visceral leishmaniasis," Int J Dermatol., Apr. 1994; 33(4), pp. 258-259 (abstract only).
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
http://ibabydoc.com/online/diseaseeczema.asp., Atopic Dermatitis, Copyright 2000.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop.
Hydroxyethylcelllulose. htt;://terpconnect.umd.edu/~choi/MSDS/Sigma-Aldrich/HYDROXYETHYL%20CELLULOSE, 5 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 2 pages.
International Search Report for International Application No. PCT/IB2006/003974, Feb. 25, 2008 (7 pages).
International Search Report, International Patent Application No. PCT/IB2007/003463, Foamix, Ltd., Jul. 18, 2008, 6 pages.
International Search Report, International Patent Application No. PCT/IB2007/003759, Foamix Ltd., Jul. 8, 2008 (7 pages).
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kathon ™ CG (product information sheet by Rohm and Haas, Jun. 2006).
Kinnunen, Contact Dermatitis Sep. 1989; 21(3): 154-8, 2 pages.
Koerber, S., "Humectants and Water Activity," Water Activity News, 2000, ISSN No. 1083-3943, 8 pages.
Leung, et al., "Bioadhesive Drug Delivery in Water-Soluble Polymers," American Chemical Society, Chapter 23, 1991, pp. 350-366.
Licking Vaginal Dryness without a Prescription. Accessed http://www.estronaut.com/a/vag_dryness.htm on Dec. 14, 2008.
Martindale, The extra pharmacopoeia [28th] edition, Eds.: Reynolds, J.E.F. and Prasad, A.B., The Pharmaceutical Press, London, pp. 862-864, 1982.

Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merriam-Webster Online Dictionaary, 2008, "Mousse," Merriam-Webster Online, Dec. 8, 2008 http://www.merriam-webster.com/dictionary/mousse, 2 pages.
Metronidazole. www.usp.org/pdf/EN/veterinary/metronidazole.pdf. accessed Sep. 10, 2009, 4 pages.
MMP Inc. International Development and Manufacturing, "Formulating specialities," http://mmpinc.com.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Office Action received from the U.S. Patent Office for U.S. Appl. No. 11/430,437, May 9, 2008, 55 pages.
Office Action received from the U.S. Patent Office, U.S. Appl. No. 11/430,599, Jul. 28, 2008, 58 pages.
OM Cinnamate. http://www.makingcosmetics.com/sunscreens/OM-Cinnamate-p102.html accessed Sep. 26, 2009, 1 page.
Pendergrass, "The shape and dimensions of the human vagina as seen in three-dimensional vinyl polysiloxane casts," Gynecol Obstet. Invest. 1996:42(3):178-82 (abstract).
Progesterone MSDS. http://www.usp.org.pdf.EN/referenceStandards/msds/1568007.pdf on Dec. 14, 2002, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-24 (abstract).
Scott as Published in Pharmaceutical Dosage Forms; Disperse Systems, vol. 3, Copyright 1998.
Shear, et al., "Pharmacoeconomic analysis of topical treatments for tinea infections," Pharmacoeconomics. Mar. 1995; 7(3); pp. 251-267 (abstract only).
Sigma Aldrich, "HLB-Numbers In Lithography Nanopatterning," http://www.sigmaaldrich.com/materials-science/micro-and-nanoelectronics/lithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Tan et al., "Effect of Carbopol and Polyvinylpyrrolidone on the Mechanical, Rheological, and Release Properties of Bioadhesive Polyethylene Glycol Gels," AAPS PharmSciTech, 2000; 1(3) article 24 (2000), 10 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.
Wormser et al., Early and topical treatment with povidone-iodine ointment reduces, and sometimes prevents, skin damage following heat stimulus, Letters to the Editor, Burns, 1998, 24, 383.
Wormser et al., Protective effect of povidone-iodine ointment against skin lesions induced by sulphur and nitrogen mustards and by non-mustard vesicants, Arch. Toxicol., 1997, 71, 165-170.
"HLB Systems", http://pharmcal.tripod.com/ch17.htm, Accessed Sep. 17, 2010, pp. 1-3.
"Reaction Rate" Accessed at en.wikipedia.org/wiki/Reaction_rate on Feb. 15, 2012. 6 pages.

(56) References Cited

OTHER PUBLICATIONS

Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation." University of Angers. Paris, France. No Date Listed. 2 pages.
Arct, et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631. 8 pages.
Austria, et al., "Stability of Vitamin C Derivatives in Solution and Topical Formulations", Journal of Pharmaceutical and Biomedical Analysis, 15:795-801 (1997). 7 pages.
Berstein, et al., Effects of the Immunomodulating Agent R837 on Acute and Latent Herpes Simplex Virus Type 2 Invections, Antimicrobial Agents and Chemotherapy, 33(9):1511-1515 (1989). 5 pages.
Blute, "Phase behavior of alkyl glycerol ether surfacants", Physical Chemistry Tenside Sur. Det., 35(3):207-212 (1998). 6 pages.
Brenes, et al., "Stability of Copigmented Anthocyanins and Asorbics Acid in a Grape Juice Model System", J. Agric Food Chem, 53(1):49-56 (2005)—Abstract, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003). 4 pages.
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology,York, Sep. 1986. pp. 668-669. 3 pages.
Burton, et al., "Hypertrichosis Due to Minoxidil", British Journal of Dermatology, 101:593-595 (1979). 3 pages.
Campos, et al., "Ascorbic Acid and Its Derivatives in Cosmetic Formulations", Cosmetics and Toiletries, 115(6):59-62 (2000)—Abstract, 1 page.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Chevrant-Breton, et al., "Etude du Traitement Capillaire <<Bioscalin>> dans les Alopecies Diffuses de la Femme", Gazette Medicale, 93(17):75-79 (1986). 5 pages.
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999). 9 pages.
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Colloidal Silica. Retrieved online on Jun. 4, 2011. <URL:http://www.grace.com/engineeredmaterials/materialsciences/colloidalsilica/default.aspx>. Copyright 2011. 2 pages.
Croda 2. Croda Cetomacrogol 1000 Product Information Sheet. 2011 (no month given). 1 page.
Croda. Aracel 165 Product Summary. 2011 (no month given). 1 page.
Dawber, et al., "Hypertrichosis in Females Applying Minoxidil Topical Solution and in Normal Controls", JEADV, 17:271-275 (2003). 6 pages.

Dentinger, et al., "Stability of Nifedipine in an Extemporaneously Compounded Oral Solution", American Journal of Health-System Pharmacy, 60(10):1019-1022 (2003)—Abstract, 1 page.
Disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224. 5 pages.
Edens, et al., "Storage Stability and Safety of Active Vitamin C in a New Dual-Chamber Dispenser", Journal of Applied Cosmetology, 17(4):136-143 (1999)—Abstract, 1 page.
Edwards, "Imiquimod in Clinical Practice", J. Am Acad Dermatol., 43(1, Pt 2):S12-S17 (2000)—Abstract, 1 page.
English machine translation of JP-08165218 (1996). 9 pages.
English translation of abstract for Japanese Patent Publication No. 4892282 (1992). 1 page.
Esposito, E. et al. "Nanosystems for Skin Hydration: A Comparative Study." International Journal of Cosmetic Science. 29. 2007. pp. 39-47. 9 pages.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Gallarate, et al., "On the Stability of Ascorbic Acid in Emulsified Systems for Topical and Cosmetic Use", International Journal of Pharmaceutics, 188:233-241 (1999). 9 pages.
Gelbard et al. "Primary Pediatric Hyperhidrosis: A Review of Current Treatment Options." Pediatric Dermatology. 2008. 25 (6). pp. 591-598. 8 pages.
Gladkikh, "Ascorbic Acid and Methods of Increasing its Stability in Drugs", Translated from Khimiko-Farmatsevticheskii Zhurnal, 4(12):37-42 (1970)—1 page.
Graves, S. et al. "Structure of Concentrated Nanoemulsions." The Journal of Chemical Physics.. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985). 5 pages.
Hallstar. Retrieved online on Jun. 4, 2011. <URL:http://www.hallstar.com/pis.php?product=1H022>. 1 page.
Harrison, et al., "Effects of cytokines and R-837, a cytokine inducer, on UV-irradiation augmented recurrent genital herpes in guinea pigs", Antivial Res., 15(4):315-322 (1991). 8 pages.
Harrison, et al., "Modification of Immunological Responses and Clinical Disease During Topical R-837 Treatment of Genital HSV-2 Infection", Antiviral Research, 10:209-224 (1988). 15 pages.
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994). 6 pages.
Heart Failure, The Merck Manual, 2008. Retrieved online at <<http://www.merck.com/mmhe/sec03/ch025/ch025a.html>> on Oct. 9, 2010. 12 pages.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.

(56) References Cited

OTHER PUBLICATIONS

International Search Report and Written Opinion for International Application No. PCT/IB10/02241 mailed Feb. 10, 2011. 9 pages.
International Search Report and Written Opinion for International Application No. PCT/IB10/02613 mailed Mar. 16, 2011. 9 pages.
International Search Report and Written Opinion for International Application No. PCT/IB10/02617 mailed Mar. 15, 2011. 10 pages.
International Search Report and Written Opinion, International Patent Application No. PCT/IB2006/004026, Foamix, Ltd., Jun. 20, 17 pages.
International Search Report from PCT/IB2006/003519, Mailed Dec. 3, 2007. 1 page.
Invitation to Pay Additional Fees for International Application No. PCT/IB2009/005012 mailed Jul. 27, 2010. 13 pages.
Izquierdo, P. et al. "Formation and Stability of Nano-Emulsions Prepared Using the Phase Inversion Temperature Method." University of Barcelona. Sep. 17, 2001. 3 pages.
Jan. "Troubled Times: Detergent Foam." http://zetatalk.com/health/theal17c.htm. Accessed Feb. 9, 2012. 2 pages.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," American Psychiatric Association Practice Guidelines (2000) pp. 1-78.
Kim, "Stability of Minoxidil in Aqueous Solution", Yakhak Hoechi, 30(5):228-231 (1986)—Abstract, 2 pages.
Kleber, M.D., H.D. et al., "Treatment of Patients with Substance Use Disorders, Second Edition," American Psychiatric Association Practice Guidelines (2006) pp. 1-276.
Kreuter, J. "Nanoparticles and microparticles for drug and vaccine delivery," J. Anat. (1996) 189, pp. 503-505. 3 pages.
Kumar, J. et ak., "Application of Broad Spectrum Antiseptic Povidone Iodine as Powerful Action: A Review," Journal of Pharmaceutical Science and Technology vol. 1(2), 2009, 48-58. 11 pages.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001. 12 pages.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Li, et al., "Solubility Behavior of Imiquimod in Alkanoic Acids", Abstract 3029, Pharmaceutical Research, vol. 14, No. 11 Supplemental (November), p. S475 (1997), 2 pages.
Lippacher, A. et al. "Liquid and Semisolid SLN Dispersions for Topical Application" Rheological Characterization. European Journal of Pharmaceutics and Biopharmaceutics. 58. 2004. pp. 561-567. 7 pages.
Lupo, "Antioxidants and Vitamins in Cosmetics", Clinics in Dermatology, 19:467-473 (2001). 7 pages.
Merck Index, An Encyclopedia of Chemicals, Drugs, and Biologicals. 13th Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Messenger, et al., "Minoxidil: Mechanisms of Action on Hair Growth", British Journal of Dermatology, 150:186-194 (2004). 9 pages.

Metz, et al., "A Phase I Study of Topical Tempol for the Prevention of Alopecia Induced by Whole Brain Radiotherapy", Clinical Cancer Research, 10:6411-6417 (2004). 7 pages.
Meucci, et al., "Ascorbic Acid Stability in Aqueous Solutions", Acta Vitaminol Enzymol, 7(3-4):147-153 (1985)—Abstract, 1 page.
Molan, Peter Clark, "World Wide Wounds: Honey as a topical antibacterial agent for treatment of infected wounds," Dec. 2001, 13 pages.
No Author Listed. "Opitmization of Nano-Emulsions Production by Microfluidization." European Food Research and Technology. vol. 225, No. 5-6. Sep. 2007. Abstract. 1 page.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007). 8 pages.
Pakpayat, et al., "Formulation of Ascorbic Acid Microemulstions with Alkyl Polyglycosides", European Journal of Pharmaceutics and Biopharmaceutics, 72:444-452 (2009). 9 pages.
Paula. http://ww.cosmeticscop.com/cosmetic-ingredient-dictionary/definition/259/c12-15-alkyl-benzoate.aspx. Printed Oct. 24, 2010. 1 page.
PCT Search Report and Written Opinion for International Application No. PCT/IB2010/001126 mailed Apr. 20, 2011, 12 pages.
Prescription Information for Aldara, Mar. 2007 (29 pages).
Prevent. (2007). In the American Heritage Dictionary of the English Language. Retrieved from http://www.credoreference.com/entry/hmdictenglang/prevent on Oct. 9, 2010. 1 page.
Psoriasis, http://www.quickcare.org/skin/causes-of0psoriasis.html. Accessed on Sept 9, 2010. 3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Raymond, "Iodine as an Aerial Disinfectant," Journal of Hygiene, vol. 44, No. 5 (May 1946), pp. 359-361. 4 pages.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Deep Cosmetics. PPG-40-PEG-60 Lanolin Oil, Retrieved at http://www.cosmeticsdatabase.com/ingredient/722972/PPG-40-PEG-60_Lanolin_Oil/?ingred06=722972 on May 19, 2010. 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

(56) References Cited

OTHER PUBLICATIONS

Sonneville-Aubrun, O. et al. "Nanoemulsions: A New Vehicle for Skincare Products." Advances in Colloid and Interface Science. 108-109.. 2004. pp. 145-149. 5 pages.
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle, et al., "Uptake of Minoxidil from a New Foam Formulation Devoid of Propylene Glycol to Hamster Ear Hair Follicles", Abstract 606, 1 page.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Wikipedia—http://en.wikipedia.org/wiki/surfactant. Accessed on Oct. 24, 2010. 7 pages.
Sweetman, Sean C. Martindale: The Complete Drug Reference. 33rd Edition. London. Pharmaceutical Press. Jun. 21, 2002. pp. 1073 and 1473 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308. 24 pages.
Tanhehco, "Potassium Channel Modulators as Anti-Inflammatory Agents", Expert Opinion on Therapeutic Patents, 11(7):1137-1145 (2001)—Abstract, 3 pages.
Tata, et al., "Penetration of Minoxidil from Ethanol Propylene Glycol Solutions: Effect of Application Volume on Occlusion", Journal of Pharmaceutical Sciences, 84(6):688-691 (1995). 4 pages.
Tata, et al., "Relative Influence of Ethanol and Propylene Glycol Cosolvents on Deposition of Minoxidil into the Skin", Journal of Pharmaceutical Sciences, 83(10):1508-1510 (1994). 3 pages.
Trofatter, "Imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle in the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994). 8 pages.
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60:751-755 (2005). 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354. 7 pages.
Williams, "Scale up of an olive/water cream containing 40% diethylene glycol momoethyl ether", Dev. Ind. Pharm., 26(1):71-77 (2000). 7 pages.
Al-Mughrabi et al., "Effectiveness of Essential Oils and Their Combinations with Aluminum Starch Octenylsuccinate on Potato Storage Pathogens," TEOP, 2013, 16(1):23-31.
Beauty Banter, "Interesting list of comedogenic ingredients!!!!!!!!!!!" QVC blog, Interesting list of comedogenic ingredients, 2014, 1-14.

Chemical Characteristics, The Olive Oil Source, © 1998-2015, retrieved on Jun. 12, 2015, http://www.oliveoilsource.com/page/chemical-characteristics, 10 pages.
Codex Standard for Olive Oils and Olive Pomace Oils Codex Stan 33-1981, Adopted in 1981, recently amended 2013, 8 pages.
Communication of a Notice of Opposition in European Application No. 03772600.7, dated Jan. 13, 2015, 36 pages.
Cremophor A Grades, BASF The Chemical Company, Jan. 2008, 6 pages.
Devos and Miller, "Antisense Oligonucleotides: Treating neurodegeneration at the Level of RNA," Neurotherapeutics, 2013, 10:486-497.
Ellis et al., "The Treatment of Psoriasis with Liquor Carbonis Detergens," J. Invest Dermatology, 1948, 10:455-459.
Griffin, "Calculation of HLB Values of Non-Ionic Surfactants," Journal of the Society of Cosmetic Chemists, May 14, 1954, 249-256.
Haw, "The HLB System: A Time Saving Guide to Surfactant Selection," Presentation to the Midwest Chapter of the Society of Cosmetic Chemists, Mar. 9, 2004, 39 pages.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Material Safety Data Sheet, Luvitol EHO, Caelo, Nov. 28, 2013, 4 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Oh et al., "Antimicrobial activity of ethanol, glycerol monolaurate or lactic acid against Listeria moncylogenes," Int. J. Food Microbiology, 1993, 20:239-246.
Permethrin (Insecticide), Wildpro, retrieved on Jun. 4, 2015, http://wildpro.twycrosszoo.org/S/00Chem/ChComplex/perm.htm, 5 pages.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Rohstoffinformationen, Hoffmann Mineral, 2008, 8 pages (with English translation).
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
United States Standards for Grades of Olive Oil and Olive-Pomace Oil, United States Dept. of Agriculture, Oct. 25, 2010, 21 pages.
WebMD, "Psoriasis Health Center," 2014, retrieved Apr. 13, 2015, http://www.webmd.com/skin-problems-and-treatments/psoriasis/psoriasis-symptoms, 3 pages.
WebMD, "Understanding Rosacea—the Basics," 2014, retrieved Apr. 13, 2015, http://www.webmd.com/skin-problems-and-treatments/understanding-rosacea-basics, 5 pages.
Williams et al., "Acne vulgaris," Lancet, 2012, 379:361-372.
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
Allantoin, Römpp Online, retrieved on Sep. 23, 2015, https://roempp.thieme.de/roempp4.0/do/data/RD-O 1-01552, 5 pages.
Coconut Oil, Wikipedia, the free encyclopedia, retrieved on Jul. 3, 2015, https://en.wikipedia.org/wiki/Coconut_oil, 8 pages.
Communication of a Notice of Opposition in European Application No. 03772600.7, dated Sep. 23, 2015, 42 pages.
Communication of a Notice of Opposition in European Application No. 03772600.7, dated Sep. 24, 2015, 30 pages.
Diethyltoluamid, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Everything but the Olive, (the Olive Oil Source 1998-2016). http://www.oliveoilsource.com/pageAchemical-characteristics).

(56) References Cited

OTHER PUBLICATIONS

Healy, "Gelled Emollient Systems for Controlled Fragrance Release and Enhanced Product Performance," Cosmetics and toiletries, 2002, 117(2): 47-54.

Lamisil, Lamisil http://www.fda.gov/downloads/Drugs/DrugSafety/PostmarketDrugSafetyInformationforPatientsandProviders/ucm052213.pdf, Published: Apr. 2001.

Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.

Mead, "Electrostatic Mechanisms Underlie Neomycin Block of the Cardiac Ryanodine Receptor Channel (RyR2)," Biophysical Journal, 2004, (87): 3814-3825.

Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.

Rowe et al., "Octyldodecanol," Handbook of Pharmaceutical Excipients, 2011, pp. 1-4, retrieved on Dec. 19, 2011, URL:http://www.medicinescomplete.com/mc/excipients/current/1001942450.htm?q=octyldodecanol&t=search&ss=text&p=1# hit.

Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.

Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-cll-mnOOO1-mnOOO1.htm?q=sucrose%20stearate&t=search&ss=text&p=3# hit.

RSES (Oil in Refrigerator Systems, Service Application Manual, 2009).

Security Datasheet, Luvitol EHO, Cetearyloctanoat, Nov. 27, 2013, 10 pages.

Suppositories?, CareCure, http://sci.rutgers.edu/forum/showthread.php?4176-Suppositories. Published: Apr. 16, 2002.

Sigma-Aldrich. http://www.sigmaaldrich.com/catalog/product/sial/p1754?lang=en® ion=. Published:Mar. 5, 2014.

Triethanolamine, haute.de, retrieved on Sep. 14, 2015, http://www.haut.de/service/inci/anzeige&id=16384&query=Triethanolamine&funktio . . . , 3 pages.

Valenta, "Effects of Penetration Enhancers on the In-vitro Percutaneous Absorption of Progesterone," J. Phann. Pharrnacol., 1997, 49: 955-959.

Wenninger et al., "International Cosmetic Ingredient Dictionary and Handbook," The Cosmetic, Toiletry, and Fragrance Association, Washington, DC., 1997, vol. 1, 4 pages.

Williams et al., "Urea analogues in propylene glycol as penetration enhancers in human skin," International Journal of Pharmaceutics, 1989, 36, 43-50.

Wu et al., "Interaction of Fatty Acid Monolayers with Cobalt Nanoparticles," Nano Letters, 2004, 4(2): 383-386.

* cited by examiner

SENSATION MODIFYING TOPICAL COMPOSITION FOAM

CROSS REFERENCE TO RELATED APPLICATIONS

This application is a continuation of co-pending U.S. patent application Ser. No. 11/971,197, filed on Jan. 8, 2008, entitled "Sensation Modifying Topical Composition Foam", which claims the benefit of priority under 35 U.S.C. §119(e) to U.S. Provisional application No. 60/879,213, filed on Jan. 8, 2007, entitled "Sensation Modifying Topical Composition Foam," both of which are incorporated in their entirety by reference.

U.S. patent application Ser. No. 11/971,197 is a continuation-in-part application of co-pending U.S. patent application Ser. No. 10/532,618, filed on Dec. 22, 2005, which is a 371 National application of International Patent Application No. IB03/005527, designating the United States and filed on Oct. 24, 2003, which claims the benefit of priority under 35 U.S.C. §119(e) to U.S. Patent Application Ser. No. 60/429,546, filed on Nov. 29, 2002, all entitled "Cosmetic and Pharmaceutical Foam," and which claims the benefit of priority under 35 USC§119(a) to Israeli Patent Application No. 152486, filed Oct. 25, 2002, all of which are hereby incorporated in their entirety by reference.

U.S. patent application Ser. No. 11/971,197 is a continuation-in-part application of co-pending U.S. patent application Ser. No. 10/911,367, filed on Aug. 4, 2004, which claims the benefit of priority under 35 U.S.C. §119(e) to U.S. Patent Application Ser. No. 60/492,385, filed on Aug. 4, 2003, both entitled "Foam Carrier Containing Amphiphilic Copolymer Gelling Agent" and both hereby incorporated in their entirety by reference.

U.S. patent application Ser. No. 11/971,197 is a continuation-in-part application of co-pending U.S. patent application Ser. No. 10/835,505, filed on Apr. 28, 2004, which claims the benefit of priority under 35 U.S.C. §119(e) to U.S. Patent Application Ser. No. 60/530,015, filed on Dec. 16, 2003, and U.S. Patent Application Ser. No. 60/492,385, filed on Aug. 4, 2003, all entitled "Oleaginous Pharmaceutical Foam" and all hereby incorporated in their entirety by reference.

BACKGROUND

Compositions of various types have incorporated within them components or agents which provide a sensation to mucosal membranes and/or to skin. The sensation may be a warming, cooling, relaxation stimulation or refreshing feeling or a combination of two or more feelings. The sensation or feeling may be real or artificial.

Compositions which include a sensation agent include, inter alia, toothpastes, mouthwashes, perfumes, lotions, shaving cream, shampoos, antiperspirants, deodorants, beverages, chewing gum, tobacco products, and pharmaceutical products.

Most compositions known to date, comprising one or more sensation agents, cannot retain the sensation at the site of application thereof in a subject over extended periods of time. Typically, topical formulations do not retain the sensational effect for more than a few seconds. Additionally, the sensation agent may be volatile, such as menthol, used for providing a topical cooling effect, and the formulation may not retain the active agent for more than a few seconds.

The mechanism of cooling and warming sensation or sensation modification for example is poorly understood at present. It has been suggested that, among other options, the action of menthol and other cooling agents and capsaicin, camphor and other heat compounds occurs via "thermoreceptors" that register "cool" and "hot" sensation, respectively. It has been suggested that the 'cooling' effect of menthol is a physiological effect due to the direct action of menthol on the nerve endings of the human body responsible for the detection of hot or cold and is not due to latent heat of evaporation such that menthol acts as a direct stimulus on the cold receptors at the nerve endings which, in turn, stimulate the central nervous system.

Substances which are known to provide a sensation of warmth or warmth modulation on application and are called "warming agents" include polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

Foams are considered a more convenient vehicle for topical delivery of active agents. There are several types of topical foams, including aqueous foams, such as commonly available shaving foams; hydroalcoholic foams, emulsion-based foams, comprising oil and water components and oleaginous foams, which consist of high oil content, and which are foamable compositions having a specific surfactant selected from the group consisting of ethoxylated lanolin oil, propoxylated lanolin oil, and mixtures thereof and high levels of water that produce fast breaking foams that disappears rapidly into the skin with cooling sensation is described. Some formulations make a sound or crackling effect when foam is dispensed. Dimethyl ether is a substance which evaporates very rapidly and its use with an aqueous non emollient gel composition, lotion composition and a solution in producing a cooling effect (as opposed to mere sensation without cooling). High levels of propellant have also been used to provide a solid or semi ointment deposit with a temperature between minus to plus 5° C.

Foam forming refrigerant compositions, suitable for emergency treatment of burns have also been described.

Foams and, in particular, foam emulsions are complicated systems which do not form under all circumstances. Changes in foam emulsion composition, such as by the addition of active ingredients may destabilize the foam. There is, therefore, a need for a foam composition, which provides desirable properties to the skin and can remain stable whilst accommodating a variety of sensation agents or active ingredients.

Formulations based on oil or ointment or emollients have a number of useful attributes making them suitable candidates for topical pharmaceutical and cosmetic compositions including foamable compositions. They are inherently stable and inert which are clearly desirable characteristics. They are able to moisturize and soften the skin and in appropriate amounts can act as a protective or barrier layer and can form a barrier to water. By appropriate formulation they can act to improve agent delivery to the skin and yet remain resistant to being washed off. On the other hand they are by their nature greasy materials and can be difficult to formulate particularly into a topical foamable composition that can deliver substantially uniform and stable composition or foam that ameliorates or overcomes the look and feel of a greasy material, especially where that composition is waterless or substantially so. It is further a problem to incorporate into such a vehicle, effective amounts of one or more active sensation and/or pharmaceutical ingredients such that they are uniformly present throughout the formulation and are effectively delivered without the use of a lower alcohol in the formulation.

On one level it is far from simple or obvious to produce waterless foamable compositions that when released produce foams of quality suitable for sensation, pharmaceutical or cosmetic application. On a further level having realized a carrier that will produce a waterless foam of quality there is an additional difficulty to be overcome, namely how to adapt the formula and achieve a formulation, which can accept a range of various active sensation, pharmaceutical and cosmetic agents such that the composition and active agent are stable and the foam produced remains of quality. Specifically, one of the challenges in preparing such waterless or substantially waterless foamable compositions is ensuring that the one or more active sensation, pharmaceutical or therapeutic agents does not react, isomerize or otherwise break down to any significant extent during is storage and use. Particularly, there remains an unmet need for improved, easy to use, stable and non-irritating foam formulations, with unique sensation, therapeutic or beneficial properties containing a stable or stabilized active sensation, pharmaceutical or cosmetic agent.

There remains an unmet need for improved, easy to use, stable and non-irritating topical foam formulations containing a stable or stabilized active sensation, pharmaceutical or cosmetic agent having a therapeutic or beneficial effect, intended for treatment of dermal and mucosal tissues.

There is still a need to provide stable aqueous and non-aqueous compositions comprising one or more sensation agents for sustained provision of at least one sensation from the sensation agent(s).

SUMMARY

The application relates to aqueous foamable vehicles capable of delivering one or more sensation agents to a body surface in a breakable foam of quality. The aqueous vehicles may be emulsion or gel vehicles. The application also relates to non aqueous foamable vehicles capable of delivering one or more sensation agents to a body surface in a breakable foam of quality. Upon contact with the body surface an effective amount of one or more sensory agents are capable of causing a perceived sensory effect.

In one or more embodiments the formulations are resistant to aging as indicated by their ability to withstand centrifugation. In other embodiments the formulations have a significant and suitable collapse time of 300 or more seconds.

In one or more embodiments the formulations are considered to be pleasant for use.

There is provided a foamable composition that is capable of producing a sensation or sensation modifying effect upon application on a body surface.

There is further provided a foamable composition that is capable of producing a sensation or sensation modifying effect upon application on a body surface, where the sensation is primarily a cooling or warming sensation over a sustained period of time. The sustained period of time is at least five minutes, more preferably, at least 15 minutes, yet more preferably, at least 30 minutes, still more preferably, at least one hour. According to some embodiments the sensation may be felt for up to two hours or more.

There is further provided a stable foamable composition that is capable of producing a sensation or sensation modifying effect upon application on a body surface, where the sensation is primarily a relaxing, soothing, stimulating or refreshing sensation.

There is provided a stable foamable composition that is capable of producing a sensation or sensation modifying effect upon application on a body surface, where the sensation is a combination of two or more sensations.

There is provided a foamable composition that is capable of producing a sensation or sensation modifying effect upon application on a body surface, in which the sensation is caused by a sensation agent and the sensation is further modulated, potentiated, increased, reduced, or ameliorated by the presence of a sensation modifying agent.

There is provided a foamable composition that is capable of producing a sensation or sensation modifying effect upon application on a body surface, in which the sensation is caused by a sensation agent and the sensation is complementary, supplementary or in addition to or superimposed on a cosmetic, therapeutic or pharmaceutical effect.

There is provided a foamable composition that is capable of producing a sensation or sensation modifying effect upon application on a body surface, wherein the foamable composition comprises a substantially non aqueous carrier.

There is provided a foamable composition that is capable of producing a sensation or sensation modifying effect upon application on a body surface, wherein the foamable composition comprises a substantially aqueous emollient carrier.

This invention relates to foamable compositions that are capable of producing a sensation or sensation modifying effect upon application on a body surface. More particularly the invention relates to foamable pharmaceutical and cosmetic compositions, containing an active agent, having a sensation or sensation modifying affect on a body surface, upon application.

There is provided a stable foamable composition that is stable on a surface at the delivery site for at least one minute, more preferably, at least two minutes, yet more preferably, for at least five minutes.

There is thus provided according to some embodiments of the present invention, a composition for providing a subject with at least one sensation at a delivery site for a sustained period of time, the composition including:
  at least one sensation or sensation modifying agent, selected from the group of
  a cooling agent;
  a warming agent;
  a relaxing or soothing agent; and
  a stimulating or refreshing agent;
  or mixtures thereof;
  a foamable carrier resistant to aging suitable for delivery of at least one sensation or sensation modifying agent; and
  a propellant at a concentration of about 3% to about 45% by weight of the total composition,
  wherein the composition is stored in an aerosol container and upon release expands to form a non-crackling short term stable foam; and
  wherein upon contact with a surface at the delivery site the prolonged sensation is not primarily due to the propellant or an exothermic reaction.

According to some embodiments, the composition does not effect a substantial temperature change to the surface.

According to some further embodiments, the cooling agent is selected from menthol; an isomer of menthol, a menthol derivative; 4-Methyl-3-(1-pyrrolidinyl)-2[5H]-furanone; WS-23, Icilin, Icilin Unilever Analog, 5-methyl-4-(1-pyrrolidinyl)-3-[2H]-furanone; 4,5-dimethyl-3-(1-pyrrolidinyl)-2[5H]-furanone; isopulegol, 3-(l-menthoxy)propane-1,2-diol, 3-(l-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, l-menthylacetic acid N-ethylamide, l-menthyl-4-hydroxypentanoate, l-menthyl-3-hydroxybutyrate, N,2,3-trimethyl-2-(1-methylethyl)-butanamide and spearmint oil.

According to some embodiments, the menthol derivative is selected from the group consisting of: menthol ethylene glycol carbonate, which is now known as Frescolat® type MGC, menthol Propylene Glycol Carbonate (Frescolat® type MPC), menthyl lactate (Frescolat ML®) and Menthone Glycerin Acetal (Frescolat MGA®) and 3-(l-Menthoxy)-1,2-propanediol.

According to some further embodiments, the warming agent is selected from polyhydric alcohols, capsaicin, capsicum powder, a capsicum tincture, capsicum extract, capsaicin, hamamalis, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol and gingeron.

According to some additional embodiments, the relaxing or soothing agent is selected from herb extracts, selected from the group consisting of aloe vera, alpha bisabolol, D-panthenol, allantoin, hamamelis, chamomile, yarrow; calendula, comfrey, witch hazel and other astringents, sea weed, and oat extracts; oils, selected from the group consisting of: almond oil, avocado oil, and comfrey; and essential oils, selected from the group consisting of: cardamone, eucalyptus, *mentha piperita* (peppermint), hyssop, and rosemary; waxy or unctuous substances selected from the group consisting of: lanolin or vaselline jelly, minerals, selected from the group consisting of: zinc oxide, calamine and selenium; vitamins, selected from the group consisting of: tocopheryl acetate (vitamin E), and pharmaceutical agents selected from the group consisting of: analgesics, anesthetics, anti-inflammatory agents, and anti-histamines, and muscle relaxants; menthol, camphor, eugenol, eucalyptol, safrol, methyl salicylate, menthyl lactate, menthyl ethoxyacetate, menthone glycerinacetal, 3-1-menthoxypropane-1,2-diol, ethyl 1-menthyl carbonate, (1S,3S,4R)-p-menth-8-en-3-ol, menthyl pyrrolidone carboxylate, N-substituted-p-menthane-3-carboxamides hamamelis extract and ginger oil.

Further provided, according to some embodiments, are compositions wherein the stimulating or refreshing agent is selected from an alcohol, L-menthol, camphor, menthe oil, capsicum extract, capsaicin, benzyl nicotinate, salicylate, glycol salicylate, acetyl choline, serotonin, histamine, a prostaglandin, a neurotransmitter; a CNS stimulant, caffeine and quinine.

In some cases, the short term stable foam is stable at the delivery site for at least one minute. In some further cases, the short term stable foam is stable at the delivery site for at least five minutes.

According to some embodiments, the sustained period of time is at least 15 minutes. According to some further embodiments, the sustained period of time is at least 30 minutes. In some further cases, the sustained period of time is at least one hour.

Further provided, according to some embodiments, are compositions, wherein the foamable carrier is at a concentration of about 40% to about 99% by weight of the total composition excluding propellant and is selected from the group consisting of an aqueous emulsion, and aqueous gel and a non aqueous carrier
wherein the carrier includes:
at least one surface active agent at a concentration of about 0.1% to about 10% by weight of the carrier;
at least one polymeric agent at a concentration of about 0.1% to about 5% by weight of the total composition; and
at least one non aqueous solvent.

According to some embodiments, the non aqueous solvent is in the case of the aqueous emulsion, a hydrophobic emollient; in the case of the aqueous gel, a penetration enhancer; and in the case of the non aqueous carrier, a polyol.

Further provided, according to some embodiments, are compositions, wherein the at least one emollient is selected from the group consisting of: avocado oil, isopropyl myristate, mineral oil; capric triglyceride, capryllic triglyceride mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane).

According to some embodiments, the at least one stabilizing surface active agent is selected from the group consisting of: stearyl alcohol; steareth-2, steareth-21; polysorbate 80, PEG-40 stearate, glyceryl monostearate, cetostearyl alcohol, laureth 4, and Ceteareth-20, or is a combination of at least two surfactants selected from the group consisting of combinations of polyoxyethylene alkyl ethers, particularly Brij 59/Brij10; Brij 52/Brij 10; Steareth 2/Steareth 20; Steareth 2/Steareth 21 (Brij 72/BRIJ 721); Myrj 52/Myrj 59; combinations of sucrose esters, particularly Surphope 1816/Surphope 1807; combinations of sorbitan esters, particularly Span 20/Span 80; Span 20/Span 60; combinations of sucrose esters and sorbitan esters, particularly Surphope 1811 and Span 60; combinations of liquid polysorbate detergents and PEG compounds, particularly Twin 80/PEG-40 stearate/methyl glucaso sequistearate.

Further provided, according to some embodiments, the at least one polymeric agent is selected from the group consisting of: locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hypromellose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose, methocel K100M, PEG 1000, PEG 4000, PEG 6000 and PEG 8000 xanthan gum; sodium carboxymethyl-cellulose, hydroxypropyl-cellulose, microcrystalline-cellulose, Avicel RC581, aluminum starch octyl succinate and a polyacrylate.

Additionally, according to some embodiments, the foamable carrier further includes one or more of the following:

a co-emulsifier or foam stabilizer at a concentration of about 0.1% to about 5% by weight of the total composition;

a wax, viscosity, bulking or firming agent at a concentration of about 0.1% to about 15% by weight of the total composition;

a co-solvent at a concentration of about 0.1% to about 20% by weight of the total composition;

a penetration enhancer or potent solvent at a concentration of about 0.1% to about 25% by weight of the total composition;

a foam adjuvant agent, selected from the group consisting of a fatty alcohol having 15 or more carbons in their carbon chain; a fatty acid having 16 or more carbons in their carbon chain at a concentration of about 0.1% to about 25% by weight of the total composition;

a stabilizer at a concentration of about 5% to about 30% by weight of the total composition; and an agent capable of having an occlusive effect at a concentration of about 5% to about 30% by weight of the total composition.

In some cases, the propellant is a cooling agent.

According to some embodiments, the composition further includes at least one additional active agent. The at least one additional active agent includes, according to some embodiments, a cosmetic active agent or a pharmaceutical active agent having a cosmetic or pharmaceutical effect other than a sensation or sensation modifying effect.

Additionally, according to some further embodiments, the at least one additional active agent is selected from the group consisting of active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, anti-yeast agents, astringents, topical cardiovascular agents, chemotherapeutic agents, cal tar, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin derivatives, vitamin A and derivatives, vitamin D and derivatives, wound healing agents and wart removers.

Further provided, according to some embodiments, are compositions, wherein the foamable carrier includes at least one carrier medium, selected from the group consisting of water, an oil, a silicone oil, an alcohol, a polyol, a polyethylene glycol (PEG), a propylene glycol, and a solvent or combinations thereof.

According to some embodiments, the foamable carrier further includes a polar solvent.

Further provided, according to some embodiments, are compositions further including an additional component selected from the group consisting of an anti-perspirant, an anti-static agent, a buffering agent, a bulking agent, a chelating agent, a colorant, a conditioner, a deodorant, a diluent, a dye, an emollient, fragrance, a humectant, moisturizer, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin.

Further provided, according to some embodiments, are compositions, wherein the sensation or sensation modifying is selected from the group consisting of:

a combination of a cooling and a warming agent;

a combination of a cooling and a soothing or relaxing agent;

a combination of a cooling and a stimulating or refreshing agent;

a combination of a warming and a stimulating or refreshing agent;

a combination of a warming and a soothing or relaxing agent;

a combination of a cooling; a warming and a soothing or relaxing agent; and a combination of a cooling; a warming and stimulating or refreshing agent.

Further provided, according to some embodiments, are compositions, wherein the propellant provides an initial cooling sensation combined with a sensation agent to provide a prolonged sensation.

Additionally, according to some embodiments, the foamable carrier further contains a foam adjuvant agent, selected from the group consisting of a fatty alcohol having 15 or more carbons in their carbon chain; a fatty acid having 16 or more carbons in their carbon chain.

Further provided, according to some embodiments, the composition includes:

the at least one sensation or sensation modifying agent including menthol in a concentration of 0.5 to about 3% by weight;

the at least one active agent includes:

coal tar extract in a concentration of around 2% up to around 20% by weight; and at least one other active agent selected from salicylic acid and hydrocortisone in a concentration of around 0.5% up to around 10% by weight; and the menthol is adapted to provide an improved sensation by ameliorating a negative sensation effect of the coal tar extract.

Further provided, according to some embodiments, are compositions, wherein:

the at least one sensation or sensation modifying agent includes menthol crystals in a concentration of 0.5 to about 3% by weight;

the at least one active agent includes:

coal tar in a concentration of around 2% up to around 20% by weight; and hydrocortisone butyrate in a concentration of around 0.5% up to around 10% by weight; and the menthol crystals are adapted to provide an improved sensation by ameliorating a negative sensation effect of the coal tar.

Additionally, there is thus provided according to some further embodiments of the present invention, a method for providing a subject with at least one sensation at a delivery site, the method including administering to the delivery site of the subject a composition including:

at least one sensation or sensation modifying agent, selected from the group of
   i. a cooling agent;
   ii. a warming agent;
   iii. a relaxing or soothing agent; and
   iv. a stimulating or refreshing agent;
   or mixtures thereof;
a foamable carrier resistant to aging suitable for delivery of at least one sensation or sensation modifying agent; and
a propellant at a concentration of about 3% to about 45% by weight of the total composition,
wherein the composition is stored in an aerosol container and upon release expands to form a non-crackling short term stable foam; and
wherein upon contact with a surface at the delivery site the prolonged sensation is not primarily due to the propellant or an exothermic reaction,
so as to provide the subject with the at least one sensation for the sustained period of time.

According to some embodiments, the method allows for the foam being stable at the delivery site for at least one minute. In some cases, the foam is stable at the delivery site for at least five minutes.

Additionally, according to some further embodiments, the method allows for the subject to sense the at least one sensation at the delivery site for at least at least 15 minutes. In some cases, the subject senses the at least one sensation at the delivery site for at least 30 minutes. In some further cases, the subject senses the at least one sensation at the delivery site for at least one hour. In yet some further cases, the subject senses the at least one sensation as increasing, peaking and decreasing over the sustained period of time.

According to some embodiments, the method allows for the subject to sense at least one sensation at the delivery site selected from a cooling sensation, a warming sensation, a heating sensation, a soothing sensation, a relaxing sensation, a stimulating sensation and a refreshing sensation.

According to some further embodiments, the administration step further includes spreading the foam over a surface at the delivery site.

According to yet some further embodiments, the delivery site is selected from the group consisting of the skin, a body cavity, a mucosal surface, the nose, the mouth, the eye, the ear canal, the respiratory system, the vagina and the rectum.

According to some embodiments, the method includes administering compositions further including at least one additional active agent. In some cases, the at least one additional active agent includes a cosmetic active agent or a pharmaceutical active agent having a cosmetic or pharmaceutical effect other than a sensation or sensation modifying effect.

According to yet some further embodiments, the at least one additional active agent is selected from the group consisting of active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, anti-yeast agents, astringents, topical cardiovascular agents, chemotherapeutic agents, cal tar, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin derivatives, vitamin A and derivatives, vitamin D and derivatives, wound healing agents and wart removers.

The method, according to some embodiments, further includes treating a disorder selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or postsurgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the at least one active agent is suitable for treating the disorder.

Thus, according to one or more embodiments, the foamable composition, includes:
   a. a foamable carrier;
   b. at least one sensation or sensation modifying agent, selected from the group of i. a cooling agent;
　　ii. a warming agent;
　　iii. a relaxing or soothing agent;
　　iv. stimulating or refreshing agent;
　　　or mixtures thereof;
　c. a propellant at a concentration of about 3% to about 45% by weight of the total composition
wherein the composition is stored in an aerosol container and upon release expands to form a foam.

In accordance with one or more embodiments, there is provided a foamable base composition for use with a sensation or sensation modifying agent comprising
　　i. a foamable carrier; and
　　ii. a propellant at a concentration of about 3% to about 45% by weight of the total composition;
wherein the composition is stored in an aerosol container and upon release expands to form a foam.

In accordance with one or more embodiments, the foamable composition further comprises at least one component, selected from the group consisting of:
　　a. a surface active agent; and
　　b. a polymeric agent;
wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.

In accordance with one or more embodiments, the foamable composition further comprises at least one component, selected from the group consisting of:
　　a. a co-emulsifier and foam stabilizer;
　　b. a viscosity, bulking or firming agent;
　　c. a stabilizer;
　　d. a co-solvent;
　　e. a penetration enhancer; and
　　f. an agent capable of having an occlusive effect.

In accordance with one or more embodiments the foamable emollient emulsion carrier composition comprises:
　　a. an aqueous carrier;
　　b. an emollient; and
　　c. a surfactant; or polymeric agent and optionally
　　d. a co-emulsifier and foam stabilizer; a viscosity, bulking or firming agent; a stabilizer; a co-solvent; a penetration enhancer and or an agent capable of having an occlusive effect
wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.

In accordance with one or more embodiments, the foamable waterless carrier composition comprises:
　　a. a non-aqueous carrier;
　　b. a surfactant; and or a polymeric agent and optionally
　　c. a co-emulsifier and foam stabilizer; and a viscosity, bulking or firming agent
wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.

DETAILED DESCRIPTION

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

There is provided a foamable composition that is capable of producing a sensation or sensation modifying effect upon application on a body surface.

There is further provided in one or more embodiments, a foamable composition that is capable of producing a sensation or sensation modifying effect upon application on a body surface, where the sensation is primarily a cooling or warming sensation.

There is further provided in one or more embodiments, a foamable composition that is capable of producing a sensation or sensation modifying effect upon application on a body surface, where the sensation is primarily a relaxing or soothing sensation.

There is further provided in one or more embodiments, a foamable composition that is capable of producing a sensation or sensation modifying effect upon application on a body surface, where the sensation is primarily a relaxing, soothing, stimulating or refreshing sensation.

There is further provided in one or more embodiments, a foamable composition that is capable of producing a sensation or sensation modifying effect upon application on a body surface, where the sensation is a combination of two or more sensations.

There is further provided in one or more embodiments, a foamable composition that is capable of producing a sensation or sensation modifying effect upon application on a body surface, in which the sensation is caused by a sensation agent and the sensation is further modulated, potentiated, increased, reduced, or ameliorated by the presence of a sensation modifying agent.

There is further provided in one or more embodiments, a foamable composition that is capable of producing a sensation or sensation modifying effect upon application on a body surface, in which the sensation is caused by a sensation agent and the sensation is complementary, supplementary or in addition to or superimposed on a cosmetic, therapeutic or pharmaceutical effect.

There is further provided in one or more embodiments, a foamable composition that is capable of producing a sensation or sensation modifying effect upon application on a body surface, wherein the foamable composition comprises a substantially non-aqueous carrier.

There is further provided in one or more embodiments, a foamable composition that is capable of producing a sensation or sensation modifying effect upon application on a body surface, wherein the foamable composition comprises a substantially aqueous emollient carrier.

There is further provided in one or more embodiments, a foamable composition that is capable of producing a sensation or sensation modifying effect upon application on a body surface, wherein the formulation is adapted so that the sensation or sensation modifying effect is of short, medium or long term duration or grades thereof.

There is further provided in one or more embodiments, a foamable composition that is capable of producing a sensation or sensation modifying effect upon application on a body surface, wherein the formulation is adapted so that onset of sensation or sensation modifying effect is of a quick, medium or slow onset or grades thereof.

There is further provided in one or more embodiments, a foamable composition that is capable of producing a sensation or sensation modifying effect upon application on a body surface, wherein the formulation is adapted so that the relative overall magnitude of sensation or sensation modifying effect is of a mild, medium or strong magnitude or grades thereof.

There is further provided in one or more embodiments, a foamable composition that is capable of producing a sensation or sensation modifying effect upon application on a body surface, wherein the sensation or sensation modifying effect increases, peaks and then decreases.

There is further provided in one or more embodiments, a foamable composition that is capable of producing a sensation or sensation modifying effect upon application on a body surface, wherein the sensation or sensation modifying effect is with no or little skin irritation.

There is further provided in one or more embodiments, a foamable composition that is capable of producing a sensation or sensation modifying effect upon application on a body surface, wherein the sensation or sensation modifying effect comprises a fragrance.

There is further provided in one or more embodiments, a foamable composition that is capable of producing a sensation or sensation modifying effect upon application on a body surface, wherein the sensation or sensation modifying effect can be useful, beneficial or therapeutic in cosmetic, toiletry, bath additive, and pharmaceutical compositions.

In one or more embodiments, the composition further contains a compatible fragrance so as for example to provide in addition aromatherapy on application of the sensation foam.

In one or more embodiments, the composition further contains a compatible washable pigment so as to provide an attractive color to the dispensed foam.

In one or more embodiments, the composition is a waterless composition with hygroscopic ingredients, which upon absorbing water present on a body surface give an initial warming sensation in addition to the prolonged sensation of the sensation agent.

It was discovered that incorporating a sensation or sensation modifying agent in a foamable composition results in a product that, when compared with the composition which is not foamed provides an improved effect.

While not wishing to be limited to any particular theory, it is presently believed that the expansion of the formulations caused by the presence of a propellant causes the product to spread in the form of a thin film on the skin or delivery site, thereby giving a soft, silky, and cosmetically elegant feel. The observed effect is analogous to a comparison between whipped cream and butter. While both of these products are produced from cream, butter is a dense, greasy water in oil emulsion, whereas whipped cream is a light air in oil emulsion in which the oil is extended over a much greater volume, thereby masking its greasy properties to a substantial extent. In the present invention, by foaming the oils with a propellant to produce a low density aerated foam, the greasy property of the oil in the formulation is ameliorated or minimized.

Moreover it was further discovered that it is possible to prepare such foamable compositions using more than one different foamable platforms or carriers. More specifically it was discovered, for example, that effective foamable compositions can be produced with a sensation or sensation modifying effect with a substantially waterless carrier and can also be produced with a substantially aqueous carrier. The ability to produce sensation or sensation modifying foam in waterless and aqueous environments allows the production of foams to suit, benefit or improve a wide variety of skin, mucosa and body cavity conditions. Based on this discovery it is possible to develop and create a multitude of foams, which provide a sensation or sensation modifying feeling with the following advantages:

1. Improvement of user compliance especially in children or sensitive patients;
2. Enhancement of user comfort;
3. Improvement of skin absorption, due to the foam texture;
4. Improvement of skin appearance due to the non-shiny appearance thereof, after administration of the composition;
5. Easier spreading on the body surface, without the need of extensive rubbing;
6. Remains substantially intact for a sufficient period to facilitate convenience of application;
7. Sensation agent may mask, neutralize, ameliorate or hide one or more undesired properties of other ingredients of the composition;
8. Improvement in absorption through skin of one or more active agents;
9. The evaporation of the propellant from newly released foam that has been applied to a body surface can, depending on the nature of the foam and the type and amount of propellant provide a cooling effect.

In accordance with one or more further embodiments, the propellant is at a concentration from about 3% to about 25% by weight of the total composition.

In accordance with one or more further embodiments, the propellant is at a concentration from about 25% to about 45% by weight of the total composition.

In accordance with one or more embodiments, the foamable base composition is flowable.

In accordance with one or more embodiments, the main carrier solvent is at a concentration of about 40% to about 90% by weight of the total composition.

In accordance with one or more embodiments, the foamable composition further comprises at least one component, selected from the group consisting of:
  a. a surface active agent;
  b. a polymeric agent wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.

In accordance with one or more embodiments, the surface active agent is a stabilizing combination of at least two surface active agents.

In accordance with one or more embodiments, the surface active agent is at a concentration of about 0.1% to about 10% by weight of the total composition.

In accordance with one or more embodiments, the polymeric agent is at a concentration of about 0.05% to about 5% by weight of the total composition.

In accordance with one or more embodiments, the surface active agent is combination of at least two surfactants.

In accordance with one or more embodiments, where the composition is an emollient emulsion the polymeric agent is preferably a combination of hydroxy propylmethyl cellulose and xantham gum. In certain other embodiments the polymeric agent is sodium carboxymethyl-cellulose, hydroxyethyl-cellulose, microcrystalline-cellulose, aluminum starch octyl succinate, and polyacrylates such as carbopol.

In accordance with one or more embodiments, wherein the composition is an emollient emulsion, the polymeric agent is preferably a hydroxypropyl-cellulose such as Klucel EF, aluminum starch octyl succinate, and polyacrylates such as carbopol.

In accordance with one or more embodiments, the co-emulsifier is at a concentration of about 0.05% to about 10% by weight of the total composition.

In accordance with one or more embodiments, the viscosity, bulking or firming agent is at a concentration of about 0.1% to about 15% by weight of the total composition.

In accordance with one or more embodiments, the stabilizer is at a concentration of about 0.1% to about 10% by weight of the total composition.

In accordance with one or more embodiments, the co-solvent is at a concentration of about 0.1% to about 30% by weight of the total composition.

In accordance with one or more embodiments, the penetration enhancer is at a concentration of about 0.1% to about 30% by weight of the total composition.

In accordance with one or more embodiments, the agent capable of having an occlusive effect is at a concentration of about 0.1% to about 30% by weight of the total composition.

In accordance with one or more embodiments, there is also provided a sensation or sensation modifying topical composition wherein the resultant foam has a density of about 0.01 to about 0.2 g/ml.

In accordance with one or more embodiments, there is also provided a sensation or sensation modifying topical composition wherein the resultant foam is a breakable foam, which if not subjected to mechanical shear break, is capable of remaining substantially intact without substantial foam collapse for about 60 seconds or more.

In accordance with one or more embodiments, there is also provided a sensation or sensation modifying topical composition wherein the resultant foam is a breakable foam, which if not subjected to mechanical shear break, is capable of remaining substantially intact without substantial foam collapse for about 120 seconds or more.

In accordance with one or more embodiments, there is also provided a sensation or sensation modifying topical composition wherein the resultant foam is a breakable foam, which if not subjected to mechanical shear break, is capable of remaining substantially intact without substantial foam collapse for about 300 seconds or more.

In an exemplary embodiment, the foamable sensation modifying topical composition is an aqueous composition, containing water and further comprises a surface active agent.

In an exemplary embodiment, the foamable sensation modifying topical composition comprises an aliphatic alcohol, water, a fatty alcohol and a surface active agent.

In an exemplary embodiment, the foamable sensation modifying topical composition is an emulsion, comprising water, a hydrophobic solvent, a surface-active agent and a polymeric agent.

Optionally, in one or more embodiments the emulsion-type foamable composition further contains a foam adjuvant agent, selected from the group consisting of a fatty alcohol having 15 or more carbons in their carbon chain; a fatty acid having 16 or more carbons in their carbon chain.

In certain embodiments, the emulsion is an oil in water emulsion, while in additional embodiments the emulsion is a water in oil emulsion.

In certain embodiments the hydrophobic carrier is an oil. Exemplary oils include mineral oil, silicone oil, a triglyceride and an ester of a fatty acid. In certain embodiments, the hydrophobic solvent is occlusive, such as petrolatum, while in other embodiments the hydrophobic carrier in non-occlusive.

In an exemplary embodiment, the foamable sensation modifying topical composition is an oleaginous foamable composition, including at least one solvent selected from a hydrophobic solvent, a silicone oil, an emollient, a polar solvent and mixtures thereof, wherein the solvent is present at a concentration of about 70% to about 96.5% by weight of the total composition, at least a non-ionic surface-active agent and at least one polymeric agent.

In an exemplary embodiment, the foamable sensation modifying topical composition includes more than 50% of a polar solvent (as used herein, the term "polar solvent" shall mean a material that produces a uniform, clear or hazy, mixture when combined with at least a weight equivalent of water), a surface-active agent and a polymeric agent.

In certain embodiments the foamable composition contains up to 80% water, while in additional embodiments the foamable composition contains up to 25% water.

In one or more embodiments, the composition is substantially alcohol free

In one or more embodiments, the composition is substantially non-aqueous.

In accordance with one or more embodiments, there is provided a method of treating, alleviating or preventing a dermatological reaction, sensation or disorder of a mammalian subject, comprising:
  a. administering an effective amount of a sensation or sensation modifying topical emollient emulsion carrier composition to a target site on a mammalian subject, comprising:
    i. an aqueous carrier at a concentration of about 40% to about 90% by weight of the total composition;
    ii. an emollient at a concentration of about 5% to about 15% by weight of the total composition;
    iii. a surfactant at a concentration of about 0.1% to about 10% by weight of the total composition;
    iv. a polymeric agent at a concentration of about 0.1% to about 5% by weight of the total composition;
    v. a propellant at a concentration of about 3% to about 45% by weight of the total composition;
    vi. at least one active agent in an effective amount which is intended to prevent, alleviate, treat or cure said reaction, sensation or disorder; and optionally;
    vii. a co-emulsifier and foam stabilizer at a concentration of about 0.1% to about 5% by weight of the total composition; a viscosity, bulking or firming agent at a concentration of about 0.1% to about 15% by weight of the total composition; a stabilizer; a co-solvent at a concentration of about 0.1% to about 20% by weight of the total composition; a penetration enhancer at a concentration of about 0.1% to about 20% by weight of the total composition; and or an agent capable of having an occlusive effect at a concentration of about 5% to about 30% by weight of the total composition;
  wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.
  b. applying mechanical shear break to the applied foam such that it is spread at, about and within the target site.

In accordance with one or more embodiments, there is provided a method of treating, alleviating or preventing a dermatological reaction, sensation or disorder of a mammalian subject, comprising:
  a. administering an effective amount of a sensation or sensation modifying topical substantially waterless foamable composition to a target site on a mammalian subject, comprising:

aa. a non-aqueous carrier at a concentration of about 40% to about 90% by weight of the total composition;
bb. a surfactant at a concentration of about 0.1% to about 10% by weight of the total composition; and or a polymeric agent at a concentration of about 0.1% to about 5% by weight of the total composition;
cc. at least one active agent in an effective amount which is intended to prevent, alleviate, treat or cure said reaction, sensation or disorder;
dd. a propellant at a concentration of about 3% to about 25% by weight of the total composition and optionally;

ee. a co-emulsifier and foam stabilizer at a concentration of about 0.1% to about 5% by weight of the total composition; and a viscosity, bulking or firming agent at a concentration of about 0.1% to about 15% by weight of the total composition.

wherein a destabilizing foam effect of the sensation or sensation modifying agent is capable of being reduced, ameliorated or countered to some extent by the introduction of a stabilizing polymer and wherein the composition is stored in an aerosol container and upon release expands to form a breakable foam.

b. applying mechanical shear break to the applied foam such that it is spread at, about and within the target site.

Hydrophobic Carrier

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer.

Polar Solvent

A "polar solvent" is an organic solvent, typically soluble both in water and oil but is not intended to characterize the solubilization capabilities of the solvent for any specific active agent or any other component of the foamable composition. The emollient emulsion and waterless formulations may contain polar solvents, which may contribute to the penetration of an active or therapeutic agent including a sensation or sensation modifying agent.

Polymeric Agent

A polymeric agent can be selected from the group consisting of locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose, carboxymethylhydroxyethylcellulose, a cationic cellulose PEG 1000, PEG1500, PEG2000, PEG 4000, PEG 6000 and PEG 8000.

Polyol

In an embodiment of the present invention, the solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol). Mixtures of polyols, including (1) at least one polyol selected from a diol and a triol; and (2) a saccharide are contemplated within the scope of the present invention.

Polyethylene Glycol

In an embodiment of the present invention, the solvent consists of a polymerized ethylene glycol, namely polyethylene glycol, which is also termed "PEG". Exemplary PEGs are provided in the following table.

| Composition | Av. Molecular weight | Appearance | Melting point (° C.) |
|---|---|---|---|
| PEG 200 | 190~210 | Oily liquid | ? |
| PEG 300 | 285~315 | Oily liquid | |
| PEG 400 | 380~420 | Oily liquid | ? |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present invention, the PEG is selected from the group consisting of PEG 200, PEG 300, PEG 400, PEG 600, PEG 1000, PEG 4000, PEG 6000 and PEG 8000. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters, of less than 12,000 CPs, and more preferably, less than 10,000 CPs.

Secondary Polar Solvent

Optionally, a secondary solvent is added to the foamable composition of the present invention. The secondary solvent is selected from a variety of organic solvents that are typically miscible on both water and oil. Examples of solvent that can be contained in the foamable carrier of the present invention include dimethyl isosorbide, tetrahydrofurfuryl alcohol polyethyleneglycol ether(glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Solubilization and Penetration Enhancement

A "skin penetration enhancer", also termed herein "penetration enhancer," is an organic solvent, typically soluble in both water and oil. Examples of penetration enhancer include polyols, such as glycerol(glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, hexylene glycol, other glycols, sulfoxides, such as dimethylsulfoxide (DMSO), dimethylformanide, methyl dodecyl sulfoxide, dimethylacetamide, dimethylisosorbide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the penetration enhancer is a polyethylene glycol (PEG) or PEG derivative that is liquid at ambient temperature In many cases, polyols, PEGs and solvents possess a high solubilizing power and thus, they can enable increased concentrations of a pharmaceutical active agent. Polyols, PEGs and solvents are also known for their skin penetration enhancement properties. These properties enable high drug bioavailability in the target area of treatment, resulting in an enhanced therapeutic effect. Occasionally, combinations of a polyol, PEGs and a secondary solvent, exhibit an increased permeability across the skin, as suggested, for example, in Eur. J. Pharm. Biopharm. 1998 November 46(3):265-71.

Thus, in one or more embodiments, the foamable carrier contains (1) at least one solvent, selected from a polyol (selected from a diol and a triol) and PEG; and (2) at least one secondary solvent.

In one or more embodiments, the foamable carrier contains (1) a mixture of at least two polyols; and (2) at least one secondary solvent. In additional embodiments, the foamable carrier contains a mixture of at least one polyol and at least one PEG; yet in other embodiments the foamable carrier contains (1) a mixture of at least one polyol and at least one PEG and (2) at least one secondary solvent.

According to certain embodiments the ratio between the polyol and/or PEG and the secondary solvent is between 9:1 and 1:1.

In certain embodiments, the polyol is selected from the group consisting of propylene glycol, hexylene glycol and glycerin (and mixtures thereof); and the secondary solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Potent Solvent

In one or more embodiments of the present invention, the foamable composition includes a potent solvent, in addition to, or in place, of one of the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments of the present invention, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition of the present invention; or even more than about 60%.

Non-limiting examples of pairs of active agent and potent solvent include: Betamethasone valerate: Practically insoluble in mineral oil (<0.01%); soluble more than 1% in glycofurol; Hydrocortisone butyrate: Practically insoluble in mineral oil (<0.01%); soluble more than 1% in glycofurol; Metronidazole: Practically insoluble in mineral oil (<0.01%); soluble more than 1% in dimethyl isosrbide; Ketoconazole: Practically insoluble in mineral oil (<0.01%); soluble more than 1% in glycofurol, propylene glycol and dimethyl isosrbide; Mupirocin: Practically insoluble in mineral oil (<0.01%); soluble more than 1% in glycofurol, hexylene glycol, dimethyl isosorbide, propylene glycol and polyethylene glycol 400 (PEG 400); Meloxicam, a nonsteroidal antiinflammatory agent: Practically insoluble in mineral oil (<0.001%); soluble in propylene glycol: 0.3 mg/mL; and in PEG 400: 3.7 mg/mL; and Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butaneediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

The use of a potent solvent in a foam composition provides an improved method of delivering poorly soluble therapeutic agents to a target area. It is known that low drug solubility results in poor bioavailability, leading to decreased effectiveness of treatment. Foam compositions of the present invention, for which the solvent includes a potent solvent, increase the levels of the active agent in solution and thus, provide high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams of the present invention, which are drip-free, provide a superior vehicle for such active agents, enabling convenient usage and accurate effective dosing.

In one or more embodiments of the present invention the present invention the foamable pharmaceutical composition may additionally include a mixture of two or more of the solvents selected from the group of hydrophobic solvents, silicone oils, emollients, polar solvents and potent solvents in an appropriate proportion as would be appreciated to a person skilled in the art.

In one or more embodiments of the present invention, the PPG alkyl ether may act as a potent solvent.

Surface Active Agent

The composition further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants can be significant in producing breakable forms of good quality. It has been further discovered that the generally thought considerations for HLB values for selecting a surfactant or surfactant combination are not always binding for emulsions and moreover for waterless and substantially non aqueous carriers the usual guidelines are less applicable. Surfactants also play a significant role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, (preferably about 7 to about 12) or more than one surface active agent and the weighted average of their HLB values is between about 7 and about 14 (preferably about 7 to about 12).

According to one or more other embodiments the composition contains a single surface active agent having an HLB value between about 9 and about 19, or more than one surface active agent and the weighted average of their HLB values is between about 9 and about 19.

In a waterless or substantially waterless environment a wide range of HLB values may be suitable.

Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values.

In an embodiment the surfactant is an ether for example polyoxyethylene (26) glycerol ether.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of ethers, like steareth 2 and steareth 21, or a pair of esters, for example, PEG-40 stearate and polysorbate 80. Ideally, the surfactants can be ethers. In certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with ether formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
|---|---|
| steareth 2 | ~4.9 |
| glyceryl monostearate/PEG 100 stearate | Av ~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

Another component of the formulations of the present invention is a compound used in the present invention is Sepigel 305. Sepigel 305 comprises Polyacrylamide and C13-14 Isoparaffin and Laureth-7. It acts as a surfactant and as a thickening and emulsifying agent, and comes in a liquid, very easy to handle form. It requires neither premixing, nor high rate of shear nor neutralisation. Sepigel 305 can be used to emulsify all types of oil phase without heating, producing gel-cream with a rich, silky texture that are easy to apply and rapidly absorbed by the skin.

More exemplary stabilizing surfactants which may be suitable for use in the present invention are found below.

PEG-Fatty Acid Monoester Surfactants, such as:

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants, such as:

| Chemical name | Product example name | HLB |
|---|---|---|
| PEG-4 dilaurate | Mapeg .RTM. 200 DL (PPG), Kessco .RTM. PEG 200 DL (Stepan), LIPOPEG 2-DL (Lipo Chem.) | 7 |
| PEG-4 distearate | Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols, such as:

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters, such as:

| Chemical name | Product example name | HLB |
|---|---|---|
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers, such as:

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4 Brij 30 (Atlas/ICI) | 9.7 |
| PEG-23 lauryl ether | laureth-23 Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants, such as:

| Chemical name | Product example name | HLB |
|---|---|---|
| Sucrose distearate | Sisterna SP50, Surfope 1811 | 11 |

Sorbitan Fatty Acid Ester Surfactants, such as:

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable formulation or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TRI or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain other embodiments the surfactant is a combination of span 60 and GMS. In certain other embodiments the surfactant is a combination of two or all of PEG 40 stearate, sorbitan stearate and polysorbate 60

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the formulation.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid. Moreover for the purposes of formulating with liquid ethers a liquid surfactant is preferred.

In one or more embodiments the liquid surfactant is a polysorbate, preferably polysorbate 80 or 60.

In one or more embodiments the at least one surface active agent is solid, semi solid or waxy. In a further embodiment they are soluble in oil and in another embodiment have a HLB of less than about 12.

It should be noted that HLB values may not be so applicable to non ionic surfactants, for example, with liquid crystals or with silicones. Also HLB values may be of lesser significance in a waterless or substantially non-aqueous environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier. In a preferred embodiment at least one surfactant is a liquid.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions of the present invention.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1.

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

For foams in selecting a suitable surfactant or combination thereof it should be borne in mind that the upper amount of surfactant that may be used may be limited by the shakability of the composition. If the surfactant is non liquid, it can make the formulation to viscous or solid. Subject to its miscibility, solid surfactants may be added first, and may require gentle warming and then cooling before being combined with the other ingredients. In general terms, as the amount of non-liquid surfactant is increased the shakability of the formulation reduces until a limitation point is reached where the formulation can become non shakable and unsuitable. Thus in one embodiment, any effective amount of surfactant may be used provided the formulation remains shakable. In other certain limited embodiments the upper limit for foamable formulations may be determined by flowability such that any effective amount can be used provided the formulation is sufficiently flowable to be able to flow through an actuator valve and be released and still expand to form a good quality foam. This may be due without being bound by any theory to one or more of a number of factors such as the viscosity, the softness, the lack of crystals, the pseudoplastic or semi pseudo plastic nature of the composition and the dissolution of the propellant into the composition.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiments the concentration of surface active agent is between about 1% and about 6% or between about 1% and about 4%.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose disterate sucrose palmitate and sucrose laurate; and alkyl polyglycosides, such as lauryl diglucoside.

Humectant

A humectant is a substance that helps retain moisture and also prevents rapid evaporation. Non limiting examples are propylene glycol, propylene glycol derivatives, glycerin, hydrogenated starch hydrosylate, hydrogenated lanolin, lanolin wax, D manitol, sorbitol, sodium 2-pyrrolidone-5-carboxylate, sodium lactate, sodium PCA, soluble collagen, dibutyl phthalate, and gelatin. Other examples may be found in the Handbook of Pharmaceutical Additives published by Gower.

Moisturizers

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Other examples may be found in the *Handbook of Pharmaceutical Additives* published by Gower.

Pharmaceutical compositions of the present invention may in one or more embodiments usefully comprise in addition a heumectant or a moisturizer or combinations thereof.

Modulating Agent

The term modulating agent is used to describe an agent which can improve the stability of or stabilize a carrier or a foamable composition and or an active agent by modulating the effect of a substance or residue present in the carrier or composition. The substance or residue may for example be acidic or basic and potentially alter an artificial pH in a waterless or substantially non aqueous environment or it may be one or more metal ions which may act as a potential catalyst in a waterless or substantially non aqueous environment or it may be an ionisation agent or it may be an oxidizing agent.

In one or more other embodiments the modulating agent is used in a waterless composition. In one or more embodiments the modulating agent is used to describe an agent which can affect pH in an aqueous solution.

The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions.

In the embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basisity balance of a waterless or substantially non aqueous carrier, composition, foamable carrier or foamable composition or resultant foam described herein.

The terms pH, pKa, and pKb, buffers such measurements and terms are artificial in a waterless environment. In an embodiment of the present invention sufficient modulating agent is added to achieve an artificial pH in which the active agent is preferably stable. Such artificial pH may be acidic, maybe basic or may be neutral.

In an embodiment of the present invention, the modulating or additional component is a pH adjusting agent or a buffering agent.

In one or more preferred embodiments of the present invention the chelating agent is selected from the group consisting of ethylenediaminetetraacetic acid ("EDTA") and salts thereof such as disodium EDTA, tetrasodium EDTA and calsium disodium EDTA; diethylenetriaminepentaacetic acid ("DTPA") and salts thereof; hydroxyethlethylenediaminetriacetic acid ("HEDTA") and salts thereof and nitrilotriacetic acid ("NTA"); more preferably EDTA, HEDTA and their salts; most preferably EDTA and its salts.

In one or more embodiments of the present invention a preferred non limiting example of the chelating agent is EDTA. Typically, the chelating and sequestering agent is present in the composition at a level of up to about 5.0%, preferably 1.0 percent, by weight, of the composition.

Combinations of Modulating Agents may be a useful for example chelating agents may be usefully used in combination with another modulating agent such as an acid, a base or a buffer system or with various combinations of modulating agents.

The modulating agent to the foamable composition of the present invention is further useful for adjusting the pH of the target area of application.

In one or more embodiments, the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. In one or more embodiments the modulating agent is a flavonoid. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

In one or more embodiments the formulations described herein may further contain a modulating agent.

Microsponges

The Microsponges are rigid, porous and spongelike round microscopic particles of cross-linked polymer beads (e.g., polystyrene or copolymers thereof), each defining a substantially noncollapsible pore network. The Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Micropnges with an aqueous carrier or with a waterless carrier described herein which may comprise a modulating agent.

Propellants

Examples of suitable propellants include volatile hydrocarbons such as butane, propane, isobutane and fluorocarbon gases, or mixtures thereof.

In an embodiment the propellant is 1681, which is a mixture of propane, isobutene and butane. In another embodiment it is AP 70, which is a mixture of propane, isobutene and butane with a higher pressure.

The propellant makes up about 5-25 wt % of the foamable composition. In some circumstances the propellant may be up to 35%. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227) 1,1, difluoro ethane (Dymel 152) and 1,1,1,3,3,3 hexafluoropropane HFCs possess Ozone Depletion Potential of 0.00 and thus, they are allowed for use as propellant in aerosol products.

In one or more embodiments, the non inflammbale propellants are used in combination with the more traditional hydrocarbon propellants.

In one or more embodiments, where Dymel is used, it is used in such levels that the sensation effect is not primarily due to the propellant.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbon propellants such as propane, isobutane and butane.

Some propellants may have a cooling effect. The evaporation of the propellant from newly released foam that has been applied to a body surface can, depending on the nature of the foam and the type and amount of propellant provide a cooling effect. In some cases the sensation is mild and in other cases the propellant can actually produce physical cooling on the skin surface. As will be appreciated such cooling effect may increase relative to the ability of the formulation to deliver increasing levels of propellant in contact with the skin.

Dimethyl ether is a product which evaporates very rapidly to produce a cooling effect and in one or more embodiments is used as part of the propellant system.

In one or more embodiments the propellant is a mixture of propane, butane and isobutene.

In one or more embodiments the propellant is a mixture of propane, butane and isobutene together with dimethyl ether.

In one or more embodiments the propellant makes up about 5-25 wt % of the foamable composition.

In certain other embodiments the amount of propellant can be increased to up to less than half of the composition, for example, where it is desired to produce a cooling effect in addition to a cooling sensation or where it is sought to produce an initial cooling effect followed by a cooling or other sensation.

Additional Components

Additional component selected from the group consisting of an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin or derivative thereof.

In addition to the sensations and sensation agents and sensation modifying effects described herein it is possible to enhance the sensation of the user and to increase compliance, by for example making the product visually attractive. Thus, in certain further embodiments the additional component is one or more of a colored active agent, a colored excipient, a pigment, a dye, a colorant and a coloring agent. Similarly, in other certain embodiments the additional component is a fragrance or fragrance masking agent Sensation or Sensation Modifying Agent The sensation modifying agent is selected from a cooling agent, a warming agent a relaxing or soothing agent; a stimulating agent; a refreshing agent; or mixtures thereof.

As will be appreciated by someone in the art two or more soothing, relaxing, cooling, stimulating, refreshing, and warming agents may be effectively combined in order to produce a combined, staggered, consecutive, overlapping, reduced or increased effect or sensation, as is appropriate.

Cooling Agents

In the context and without degradating from explanations given elsewhere, substances, which are known to provide a "cool" sensation or cooling effect on or following application to a body surface; and substances that, on or following topical application can ameliorate a hot sensation or a heating effect are called "cooling agents". Any agent which, when incorporated in the foamable composition in a concentration sufficient to exert a cooling sensation or effect or to ameliorate a hot sensation or heating effect, is suitable for use a cooling agent in accordance with the present invention. The cooling agent may be an excipient, an active ingredient or pharmaceutical, therapeutic or cosmetic agent or a propellant or combinations of two or more agents.

Hence, non limiting examples of cooling agents, which are all incorporated herein by reference are provided in U.S. Pat. Nos. 3,419,543, 4,020,153, 4,032,661, 4,033,994, 4,034,109, 4,059,118, 4,060,091, 4,070,449, 4,070,496, 4,136,163, 4,150,052, 4, 4,153,679, 157,384, 4,178,459, 4,193,936, 4,226,988, 4,230,688, 4,296,255, 4,459,425, 5,266,592, 5,608,119, 5,725,865, 5,773,410, 5,843,466, 5,959,161, 6,214,788, 6,267,974, 6,303,817, 6,328,982, 6,359,168, 6,482,983, 6,592,884, 6,884,906 and 7,030,273 US Patent Application 20040067970, DE 2,202,535, DE 2,205,255, DE 2,503,555, DE 2,608,226, DE 4,226,043, GB 1,351,761, GB 1,351,762, GB 1,421,744, JP 2004059474 and WO 2005049553; and in Watson et al, J. Soc. Cosmet. Chem. 29, 185-200 (1978); and Ottinger et al in J. Agric. Food Chem., 49, 5383-5390 (2001).

In an embodiment, the cooling agent has a further sensation or sensation modifying feeling or effect.

In an embodiment, the cooling agent is menthol. In additional embodiment, the cooling agent is an isomer or a derivative of menthol, as exemplifies in the following schemes:

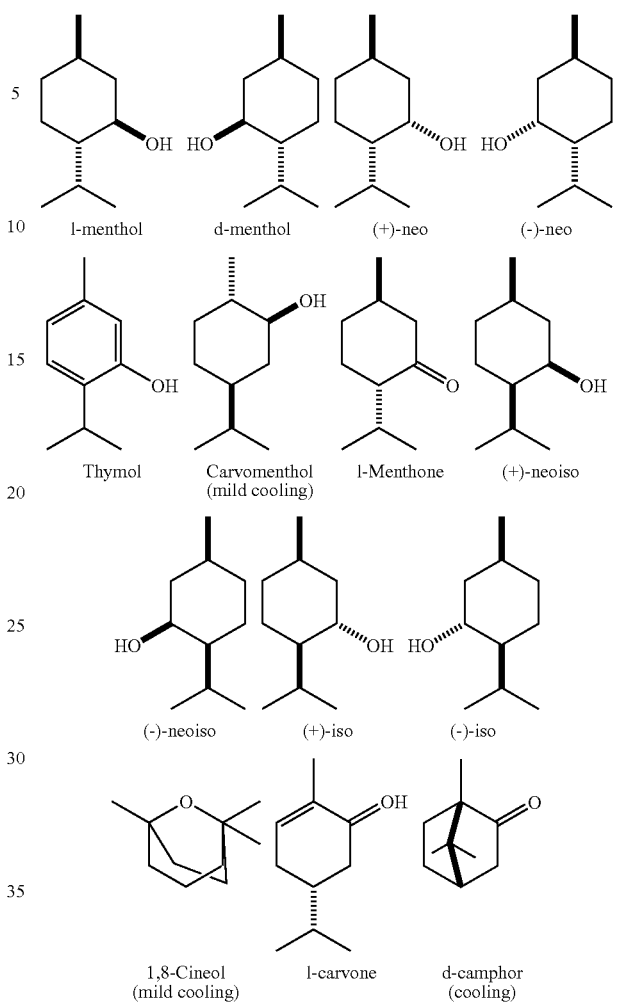

Additional examples of menthol derivatives are monomenthyl esters of di- and polycarboxylic acids:

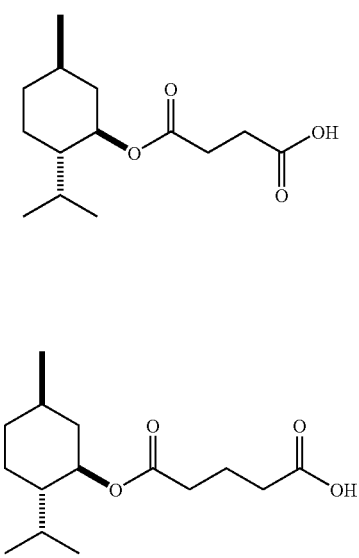

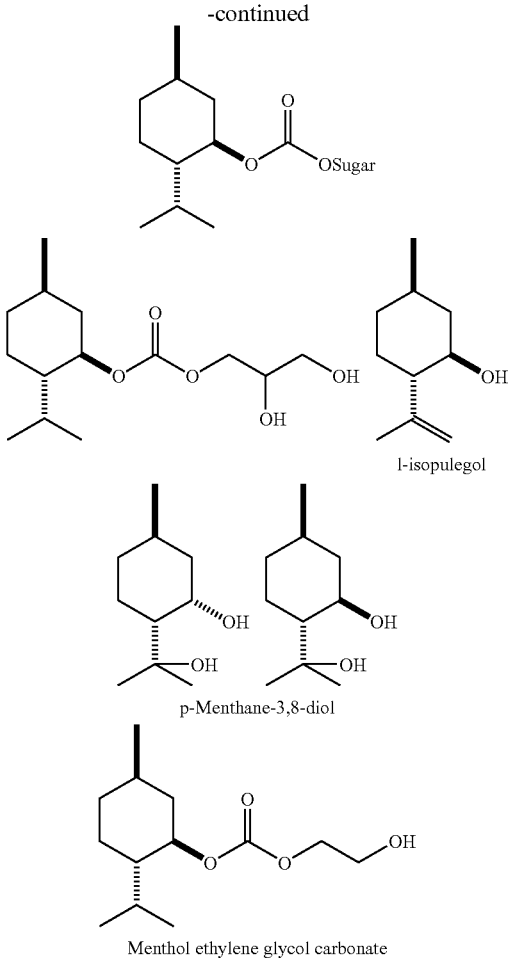

l-isopulegol p-Menthane-3,8-diol

Menthol ethylene glycol carbonate

Some derivatives have been developed to be substantially without smell.

Useful exemplary menthol derivatives are menthol ethylene glycol carbonate, which is now known as Frescolat® type MGC, enthol Propylene Glycol Carbonate (Frescolat® type MPC), menthyl lactate (Frescolat ML®) and Menthone Glycerin Acetal (Frescolat MGA®).

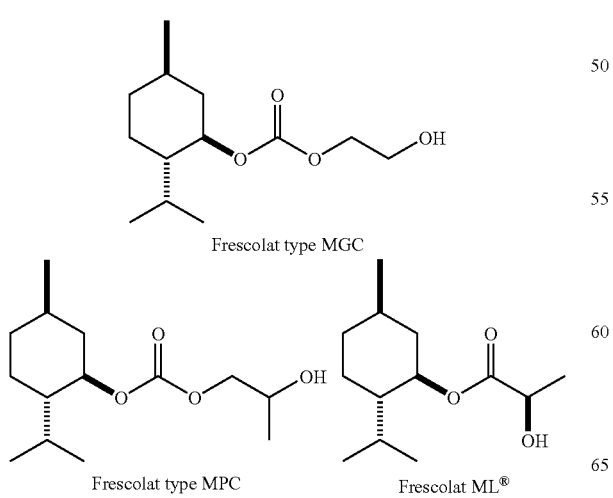

Frescolat type MGC

Frescolat type MPC     Frescolat ML®

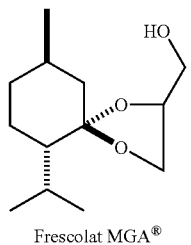

Frescolat MGA®

Additional widely used menthol derivatives are 3-(l-Menthoxy)-1,2-propanediol, known as Cooling Agent 10; and the same structure with an additional methyl group in the glycerin part of the molecule:

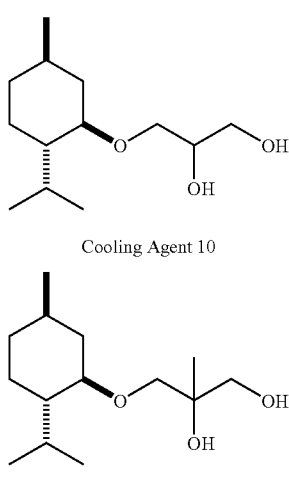

Cooling Agent 10 l-Menthoxy-2-methyl 1,2-propanediol

Menthoxy-coolants are additional cooling menthol derivatives:

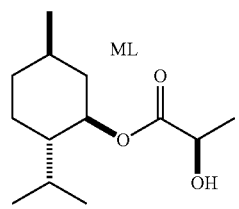

3748

ML

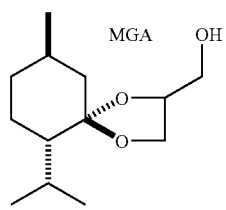

3807

MGA

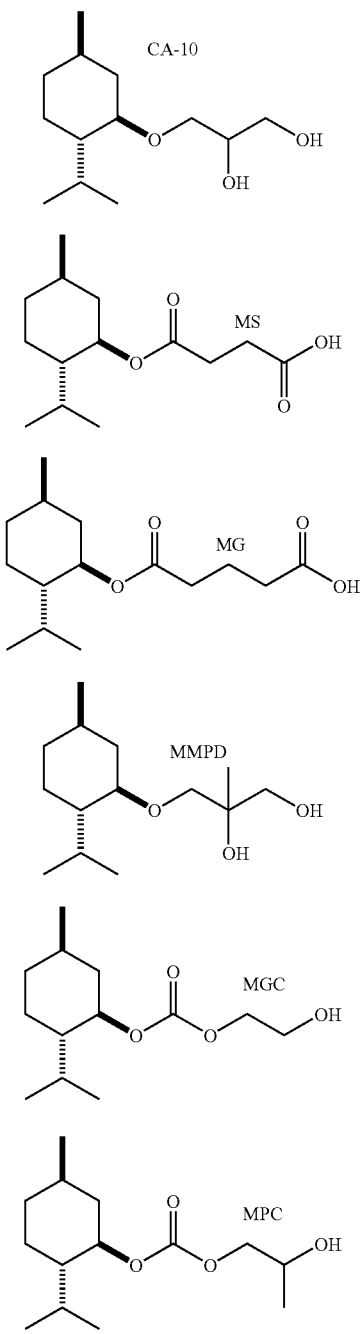

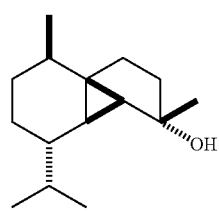

Cubebol is an example of a coolant with a C—C bond in the 3d position of p-menthane.

Cooling agents, which are not menthol derivatives, are also suitable for use in accordance with the present invention. Examples of such cooling agents are provided below:

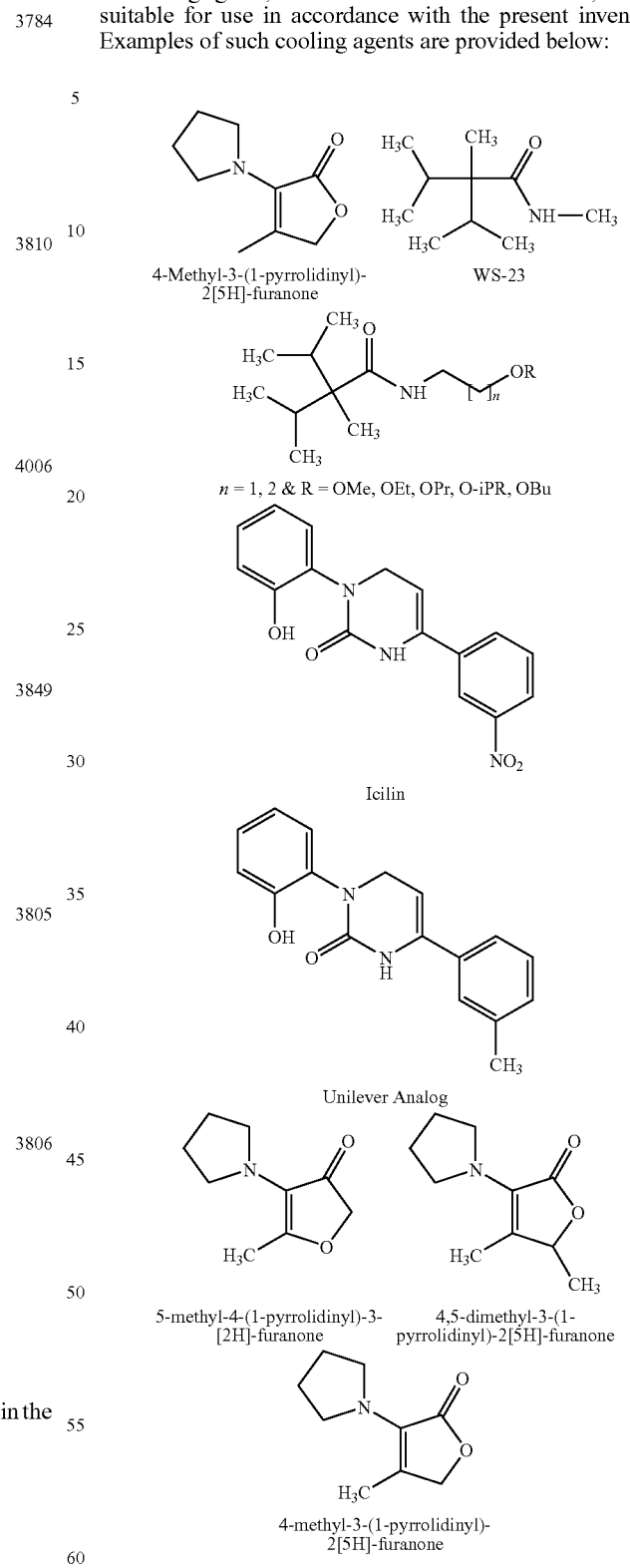

Exemplary cooling agents which can be used in the invention include, but are not limited to, menthol, isopulegol, 3-(l-menthoxy)propane-1,2-diol, 3-(l-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate and its alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, l-menthylacetic acid N-ethylamide, l-menthyl-4-hydroxypentanoate, l-menthyl-3-hydroxybutyrate, N,2,3-trimethyl-2-(1-methylethyl)-butanamide, and spearmint oil.

The cooling agent is incorporated in the composition in a concentration which, on one side is safe and on the other side provides a cooling sensation or cooling effect upon application of the cooling foamable composition onto a body surface.

In an embodiment, the cooling agent also possesses therapeutic properties. For example, menthol is being used in the therapy of psoriasis; relief of nasal complaints and sore throats; and WS-3 (N-Ethyl-p-menthane-3-carboxamide) and related N-substituted p-menthane carboxamides, as well as p-Menthane-3,8-diols are known insect repellents Warming Agents In the context and without degrading from explanations given elsewhere, substances, which are known to provide a warming sensation or warming effect on or following application to a body surface; and substances that, upon or following topical application can ameliorate a cold sensation or a cooling effect are called "warming agents". Any agent which, when incorporated in the foamable composition in a concentration sufficient to exert a warming sensation or warming effect or to ameliorate a cold sensation or cooling effect, is suitable for use a warming agent in accordance with the present invention. The warming agent may be an excipient, an active ingredient or pharmaceutical, therapeutic or cosmetic agent or combinations of two or more agents.

Exemplary substances, which are known to provide a sensation of warmth on application and called "warming agents". include polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives (JP-A-57-9729), such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

The warming agent is incorporated in the composition in a concentration which, on one side is safe and on the other side provides a warming sensation or warming effect upon application of the warming foamable composition onto a body surface.

In an embodiment, the warming agent also possesses therapeutic properties. For example, capsicum powder, capsicum tincture and extract, as well as capsaicin and homocapsaicin are used for topically treating muscle and joint pain.

Combination of a Cooling Agent and a Warming Agent

It is also possible to modulate, potentate, increase, reduce, or ameliorate the sensation effect by introducing into the composition a sensation modifying agent. Thus, the sensation effect or sensation induced by a first sensation or sensation modifying agent maybe reduced by addition of a second sensation or sensation modifying agent in the composition. For example, the cooling sensation of a cooling formulation may be reduced by the presence of a warming or warming modifying agent. Likewise, the warming sensation of a warming formulation may be reduced by the presence of a cooling or cooling modifying agent. Thus in one exemplary embodiment the composition comprises an effective amount of cooling peppermint oil and a lesser effective amount of capsaicin warming agent such that the cooling sensation is the predominant sensation. In another exemplary embodiment the composition comprises an effective amount capsaicin of and a lesser effective amount of peppermint oil cooling agent such that the warming sensation is the predominant sensation. In another embodiment the cooling and warming agents are selected so that the cooling and warming effects or sensations are staggered. For example, in one exemplary embodiment the composition comprises an effective amount capsaicin of and an effective amount of dimethyl ether cooling agent such that the cooling sensation is the initial predominant sensation and the warming sensation follows on as the subsequent predominant sensation. Other cooling and warming agents may be effectively combined as will be appreciated by someone in the art in order to produce a combined, staggered, consecutive, overlapping, reduced or increased effect or sensation, as is appropriate.

Soothing or Relaxing Agents

There are many different categories of agents which have a soothing effect and which may be used in the present invention in an effective amount either on their own or in combination with an effective amount of other soothing agents or in combination with an effective amount of other sensation or sensation modifying agents as will be appreciated by someone in the art in order to produce a combined, staggered, consecutive, overlapping, reduced or increased effect or sensation, as is appropriate.

Non limiting examples of soothing agents are herb extracts, such as, aloe vera, alpha bisabolol, D-panthenol, allantoin, hamamelis, chamomile, yarrow; calendula, comfrey, witch hazel and other astringents, sea weed, and oat extracts; oils, such as, almond oil, avocado oil, and comfrey; and essential oils, such as, cardamone, eucalyptus, *mentha piperita* (peppermint), hyssop, and rosemary; waxy or unctuous substances such as lanolin or vaselline jelly, minerals, such as, zinc oxide, calamine and selenium; vitamins, such as, tocopheryl acetate (vitamin E), and drugs, such as, analgesics, anesthetics, anti-inflammatory agents, and anti-histamines, muscle relaxants and the like.

Other non limiting examples are menthol, camphor, eugenol, eucalyptol, safrol, methyl salicylate, menthyl lactate, menthyl ethoxyacetate, menthone glycerinacetal, 3-l-menthoxypropane-1,2-diol, ethyl l-menthyl carbonate, (1S, 3S,4R)-p-menth-8-en-3-ol, menthyl pyrrolidone carboxylate, N-substituted-p-menthane-3-carboxamides (as described in U.S. Pat. No. 4,136,163, which is incorporated herein by reference) and ketal coolants (as described in WO 93/23005, which is also incorporated herein by reference) including, for example, l-menthon-ld-isomenthon glycerin ketal.

In one exemplary embodiment the composition comprises an effective amount of soothing hamamelis and a lesser effective amount of frescolate cooling agent such that the soothing sensation is the predominant sensation. In another exemplary embodiment the composition comprises an effective amount capsaicin of and a lesser effective amount of hamamelis soothing agent such that the warming sensation is the predominant sensation. In another embodiment, the soothing and warming agents are selected so that the soothing and warming effects or sensations are staggered or partially overlapping. In another embodiment, the soothing and cooling agents are selected so that the soothing and cooling effects or sensations are staggered or partially overlapping.

Stimulating or Refreshing Agents

There are many different categories of agents which have a stimulating or refreshing sensation or effect and which may be used in the present invention in an effective amount either on their own or in combination with an effective amount of other stimulating or refreshing agents or in combination with an effective amount of other sensation or sensation modifying agents as will be appreciated by someone in the art in order to produce a combined, staggered, consecutive, overlapping, reduced or increased effect or sensation, as is appropriate.

Non limiting examples are alcohols, L-menthol, camphor, menthe oil, capsicum extract, capsaicin, benzyl nicotinate, salicylate, glycol salicylate, acetyl choline, serotonin, histamine, prostaglandins, other neurotransmitters; CNS stimulants; caffeine, quinine, and the like might be suitable stimulants in dosages or delivery systems where they essentially or primarily have a local or topical as opposed to systemic effect.

Specific Agents

Ginger

Ginger is said to have several pharmacological activities, including anti-emetic, antithrombotic, antimicrobial, anticancer, antioxidant and anti-inflammatory properties. Also, ginger has been reported to have hypoglycaemic, hypo- and hypertensive, cardiac, prostaglandin and platelet aggregation inhibition, antihypercholesterolaemic, cholagogic and stomachic properties. Ginger has carminative properties and has also been tried for the prophylaxis of motion sickness and nausea and vomiting in pregnancy. In vitro studies have demonstrated that constituents of ginger, such as 6-, 8- and 10-gingerols and galanolactone, have antiserotonergic activity. Ginger oil is used in aromatherapy.

Capsicum

The capsaicinoids are principally responsible for the biological activity of capsicum. These pungent principles are thought to stimulate and aid digestion and to act as a counter-irritant when applied externally. Capsaicin has also been used as a neurochemical tool for studying sensory neurotransmission. Topical creams containing capsaicin 0.025% and 0.075% are used for symptomatic relief of osteoarthritis, and post-herpetic neuralgia, respectively. Capsicum oleoresin and capsaicin are ingredients of a number of over-the-counter topical preparations for relief of pain in muscle, tendon and joints. Capsaicin has effects on nervous, cardiovascular, respiratory, thermoregulatory and gastrointestinal systems. Capsaicin has been used as a neurochemical tool for studying sensory neurotransmission.

Hamamelis

Witch hazel is characterized by its tannin constituents and astringent properties. It is also said to have haemostatic properties. The documented herbal uses are related to these astringent properties. It has been used topically in the treatment of haemorrhoids, eczema and dermatitis. Vasoconstriction was reduced in the hindquarters of rabbits. A fraction of an aqueous ethanolic bark extract was significantly active against herpes simplex virus type 1 (HSV-1). Topical applications of a hydroglycolic extract of witch hazel leaf reduced skin temperature perhaps due to a vasoconstrictor effect. After-sun lotion containing 10% hamamelis was reported to have suppressed erythema.

Peppermint Oil

Peppermint oil is an aromatic carminative that relaxes gastrointestinal smooth muscle and relieves flatulence and colic. Peppermint oil is also used with other volatile agents in preparations for respiratory-tract disorders. It is also used in aromatherapy.

Menthol

Menthol is chiefly used to relieve symptoms of bronchitis, sinusitis, and similar conditions. For this purpose it may be used as an inhalation, usually with benzoin or eucalyptus oil, as pastilles, or as an ointment with camphor and eucalyptus oil for application to the chest or. When applied to the skin menthol dilates the blood vessels, causing a sensation of coldness followed by an analgesic effect. It relieves itching and is used in creams, lotions, or ointments in pruritus and urticaria. It has also been applied to the forehead, presumably as a counter-irritant, for the relief of headache. Menthol has a carminative action.

(Sources: Matindale and Herbal Extracts Electronic Edition 2008)

Additional Active Agent

The foamable carrier is an ideal vehicle for active pharmaceutical ingredients and active cosmetic ingredients. In the context herein, active pharmaceutical ingredients and active cosmetic ingredients are collectively termed "additional active agent" or "additional active agents".

Suitable additional active agents include but are not limited to active herbal extracts, acaricides, age spot and keratose removing agents, allergen, analgesics, local anesthetics, anti-acne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin derivatives, vitamin A, vitamin A derivatives, vitamin D, vitamin D derivatives, flavanoids, wound healing agents and wart removers. As is known to one skilled in the art, in some instances a specific active agent may have more than one activity, function or effect.

Fields of Applications

The foamable composition is suitable for treating any inflicted surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

A sensation modifying foamable composition can be used in any condition that can benefit from the modification of a cold or warm sensation, and in any condition that can benefit from stabilizing a cold or warm sensation, by applying a cooling or a warming foam on the target site.

Examples of uses of a cooling foam composition include:
Treatment of over-heated body surface;
Treatment of the skin after sun-burn;
Treatment of the skin after blistering;
Treatment of the skin after radiation treatment, burn or injury;
Treatment of the skin after friction burn;
Treatment of the skin after inflammation;
Treatment of the skin after insect bite or sting;
Treatment of the skin after shaving;
Treatment of the skin after hair removal;
Treatment of the skin after laser treatment, burn or injury;

Treatment or preparation of the skin prior to radiation, laser, or heat treatment or hair removal;
Treatment of the skin after, during or before acupuncture;
Treatment of the skin after or during stress;
Treatment of the skin upon pain.

Examples of uses of a warming foam composition include:
Treatment of over-cooled body surface;
Treatment of the skin after exposure to cold environment;
Treatment of the skin with inadequate circulation;
Treatment of the skin after wind exposure;
Treatment of the skin after liquid gas treatment, burn, or injury;
Treatment or preparation of the skin prior to liquid gas treatment;
Treatment of the skin after, during or before massage;
Treatment of the skin after or during stress.

By selecting a suitable sensation modifying agent, or a combination of at least two sensation modifying agents, or a combination of at lease one sensation modifying agent and at least one additional therapeutic agent, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn.

The composition is also suitable for administering a hormone to the skin or to a mucosal membrane or to a body cavity, in order to deliver the hormone into the tissue of the target organ, in any disorder that responds to treatment with a hormone.

Higher (Fatty) Alcohols

In some embodiments of the present invention, the compositions and carriers comprise one or more higher alcohols. These generally exclude "lower alcohols". The fatty alcohols are typically liquid at ambient temperature.

Fatty alcohols may defined as follows:

The fatty alcohols hereof have a melting point of 30° C. or less, preferably about 25° C. or less, more preferably about 22° C. or less.

The unsaturated fatty alcohols hereof are also nonvolatile. By nonvolatile what is meant is they have a boiling point at 1.0 atmospheres of at least about 260° C., preferably at least about 275° C., more preferably at least about 300° C.

Suitable fatty alcohols include unsaturated monohydric straight chain fatty alcohols, saturated branched chain fatty alcohols, saturated C8-C12 straight chain fatty alcohols, and mixtures thereof. The unsaturated straight chain fatty alcohols will typically have one degree of unsaturation. Di- and tri-unsaturated alkenyl chains may be present at low levels, preferably less than about 5% by total weight of the unsaturated straight chain fatty alcohol, more preferably less than about 2%, most preferably less than about 1%.

Preferably, the unsaturated straight chain fatty alcohols will have an aliphatic chain size of from C12-C22, more preferably from C12-C18, most preferably from C16-C18. Especially preferred alcohols of this type include oleyl alcohol and palmitoleic alcohol.

The branched chain alcohols will typically have aliphatic chain sizes of from C12-C22, preferably C14-C20, more preferably C16-C18. Exemplary branched chain alcohols for use herein include isostearyl alcohol, octyl dodecanol, and octyl decanol. Examples of saturated C8-C12 straight chain alcohols include octyl alcohol, caprylic alcohol, decyl alcohol, and lauryl alcohol. Furthermore, the higher alcohols may be selected from straight chain fatty alcohols, having 6 or more carbon atoms, which are liquid at ambient temperature, such as, but not limited to Hexanol, Octanol, Nonanol, Decanol; branched alcohols, such as: 2 Octanol (Capryl Alcohol), Undecanol (Undecyl Alcohol), 2 Butyl Octanol (Isolauryl Alcohol), Tridecyl Alcohol (Isotridecyl Alcohol), 2 Butyl Decanol, 2 Hexyl Octanol, Isomyristyl Alcohol, 2 Hexyl Decanol, Isocetyl Alcohol, 2 Octyl Decanol, 2 Hexyl Dodecanol, Isostearyl Alcohol, Isooctadecanol, Isooleyl Alcohol (unsaturated and branched), Isoarachidyl Alcohol, 2 Decyl Tetradecanol, Isolignoceryl Alcohol, 2 Decyl Tetradecanol, 2 Tetradecyl Octadecanol, 2 Tetradecyl Eicosanol, 2 Hexadecyl Octadecanol, 2 Hexadecyl Eicosanol; additionally unsaturated alcohols, such as Erucyl Alcohol, Linoleyl Alcohol, oleyl alcohol may be employed.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or solvents due to their skin-irritating effect. Thus, the composition is substantially alcohol-free and includes less than about 5% final concentration of lower alcohols, preferably less than about 2%, more preferably less than about 1%.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. patent application Ser. No. 11/732,547, filed on Apr. 4, 2007, KERATOLYTIC ANTIFUNGAL FOAM; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. patent application Ser. No. 11/825,406, filed on Jul. 5, 2007, entitled DICARBOXYLIC ACID FOAMABLE VEHICLE AND PHARMACEUTICAL COMPOSITIONS THEREOF; U.S. patent application Ser. No. 11/900,072, filed on Sep. 10, 2006, entitled FOAMABLE VEHICLE AND VITAMIN AND FLAVONOID PHARMACEUTICAL COMPOSITIONS THEREOF; and U.S. patent application Ser. No. 11/947,751, filed Nov. 29, 2007, entitled COMPOSITIONS WITH MODULATING AGENTS, all of which are incorporated herein by reference in their entirety. More particularly any of the active ingredients; the solvents; the surfactants; foam adjuvants; polymeric agents, penetration enhancers; preservatives, humectants; moisturizers; and other excipients as well as the propellants and methods listed therein can be applied herein and are incorporated by reference.

The invention is described with reference to the following examples. This invention is not limited to these examples and experiments. Many variations will suggest themselves and are within the full intended scope of the appended claims.

Methodology

The formulas of the present invention may be made in the following general way with appropriate adjustments for each formulation as will be appreciated by someone skilled in the art. Polymers, if any, are mixed, swelled and solubilized in the waterless medium, when necessary, with appropriate heat until it forms a clear solution. Stabilizing surfactants added usually with heat, until a homogeneous mixture is obtained, the mixture is then allowed to cool. The remainder of the ingredients, are then added with mixing until they have dissolved in the medium. The active agent is usually added at the end once the modulating agent, if present, has been incorporated. For foam the canisters are then filled with the above waterless formula, sealed and crimped with a valve and pressurized with the propellant.

A general procedure for preparing foamable compositions is set out in WO 2004/037225, which is incorporated herein by reference.

Composition and Foam Physical Characteristics and Advantages

A pharmaceutical or cosmetic composition manufactured using the foamable carrier of the present invention is very easy to use. When applied onto the body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of at least one year, or preferably, at least two years at ambient temperature, as revealed in accelerated stability tests or aging tests. In certain embodiments a product may satisfy stability tests if upon light shaking a homogenous formulation is restored and remains stable until well after dispensing. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Quantitative and Qualitative Tests

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, or occasionally FG, when released from the aerosol container. Smaller bubbles are indicative of more stable foam, which does not collapse spontaneously immediately upon discharge from the container. The finer foam structure looks and feels smoother, thus increasing its usability and appeal.

Foam Physical Characteristics

In terms of foam consistency and texture an acceptable foam is one, that exhibits the following characteristics:

A "stable foam" is defined herein as a composition, which upon release from an aerosol can, creates a foam mass, which is sustained on a surface for at least one minute, more preferably at least two minutes, and yet more preferably for at least 5 minutes. A period of minutes is regarded as a short term, but nevertheless it allows a good and more than sufficient period of time for a subject to receive foam dispensed on a body surface and to spread it or to transfer it to another region and to spread it.

Foam texture should vary from a very fine creamy foam to a fine bubble structure.

Foam has to have specific gravity in the range of about 0.02 gr/mL to about 0.5 gr/mL, more preferably between about 0.04 gr/mL and about 0.2 gr/mL.

In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties an acceptable foam is one, that: creates a pleasant feeling after application; leaves minimal oily residue; and leaves minimal shiny residual look.

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam of the present invention is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Foam Collapse

A further aspect of the foam is breakability. Thermally sensitive foams immediately collapse upon exposure to skin temperature and, therefore, cannot be applied on the hand and afterwards delivered to the afflicted area.

The foam of the present invention has several notable advantages, when compared with hydroalcoholic foam compositions, such as Breakability. The foam of the present invention is thermally stable and breakable under sheer force but is not "quick breaking which allows comfortable application and well directed administration to the target area.

Skin drying and skin barrier function. Short chain alcohols are known to dry the skin and impair the integrity of the skin barrier. By contrast, including a film forming agent in the composition of the present invention foes not cause unwanted skin barrier damage.

Irritability. Due to the lack of lower alcohols (C1-C5) and improvement in skin barrier function, skin irritability is eliminated.

Another property of the foam is specific gravity, as measured upon release from the aerosol can. Typically, foams have specific gravity of less than 0.12 g/mL; less than 0.10 g/mL; or less than 0.08 g/mL, depending on their composition and on the propellant concentration.

EXAMPLES

The invention is described with reference to the following examples. This invention is not limited to these examples and experiments. Many variations will suggest themselves and are within the full intended scope of the appended claims All % values are provided on a weight (w/w) basis.

In some cases the formulations are expressed in amounts up to 100% including the propellant. In other cases the formulations are expressed in amounts up to 100% not including the propellant, which is then added to the composition.

General Methodology

In one or more various embodiments the sensation or sensation modifying topical compositions can be prepared according to the general methodology set out below with appropriate changes as would be well appreciated by a man of the art.

Emulsion Foam
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly internal phase to external phase at 75° C. under vigorous mixing and homogenize to obtain fine emulsion.
5. Cool to below 40° C. and add sensitive ingredients with mild mixing.
6. Cool to room temperature.

This methodology is suitable, for example, for the preparation of the hamamelis, and also for the capsaicin emollient emulsion compositions exemplified below.

Waterless Foam
1. Dissolve the polymers in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

This methodology is suitable, for example, for the preparation of the capsaicin waterless compositions exemplified below.

Emulsion: Mint Oil
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add internal phase to external phase at 75° C. under vigorous mixing and homogenize to obtain fine emulsion.
5. Cool to below 40° C.
6. Add sensitizing agents and any other active ingredient with mild mixing.
7. Cool to room temperature.
8. In case of Pemulene® stabilizer, dissolve the Pemulene® in the Mint oil and add to the emulsion.

Waterless: Mint Oil
1. Dissolve the polymers in the main solvent with heating or cooling as appropriate for specific polymer. Add the all other ingredients and heat to 75° C. to melt and dissolve the various ingredients.
2. Cool to below 40° C.
3. Add sensitizing agents and any other active ingredient with mild mixing.
4. Cool to room temperature.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with PFF and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing
Propellant Filling

Pressurizing is carried out using a hydrocarbon gas or gas mixture. Canisters are filled and then warmed for 30 sec in a warm bath at 50° C. and well shaken immediately thereafter.

Closure Integrity Test.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Foam Tests

By way of non limiting example the objectives of hardness, collapse time and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC (Freeze Thaw Cycles)

To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at 5° C., at 25° C., at, 40° C. and at 50° C. At appropriate time intervals canisters are removed and the amount of active agent in the foam sample is measured.

Creaming by Centrifugation
Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.

Procedure

Following preparation of the experimental formulation/s, allow to stand at room temperature for ≥24 h. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.

Transfer each mixture to 1.5 mL microtubes. Tap each microtube on the table surface to remove entrapped air bubbles.

Place visually balanced microtubes in the centrifuge rotor and operate the centrifuge at one or more of 10,000 rpm for 10 min, 3,000 rpm for 10 min or at 1,000 rpm for 10 min.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40× Camera (resolution 10 MP) equipped with Sigma Macro Lens (ref: APO MACRO 150 mm F2.8 EX DG HSM). Pictures obtained are cropped to keep a squared region of 400 pixels×400 pixels.

Foam Satisfaction Tests

Compositions of the present invention were separately applied to clean skin of a group of human subjects. After 5 minutes tested subjects were asked to provide a gauge of their satisfaction relating to the following parameters: Ease of application, skin absorption, stickiness, odor, oily residue, skin surface shiny appearance, composition stability; overall satisfaction; sensation change, such as cooling, relaxing, heating etc. The subjects gauged their response according to the following scoring system:
1—very bad feeling
2—Bad feeling
3—feels "OK"
4—Feels good
5—Feels excellent, want more The scores assigned by the subjects were added and an average result was recorded.

Sensation Quantification Tests

In cases where a sensation agent was added to the composition, the above test was repeated after 15, 30, 60, 120 minutes and after washing off the composition from the skin surface (after 120 minutes). The subjects were asked to gauge their feeling of a sensation, such as sensation change, such as cooling, relaxing, heating etc. The scores assigned by the subjects were added and an average result was recorded.

In some cases, as exemplified below, the sensation was observed over a prolonged or sustained period of time.

By "prolonged period of time" or "sustained period of time" or "substantial period of time" (used interchangeably herein), is meant a period of time of about five or more minutes, more typically, at least 15 minutes in which the subject senses a sensation pertaining to a sensation agent applied to a target or delivery site on/in the subject.

Foam Temperature Effects

In the Examples hereinbelow, the following test was performed to see if there were any temperature changes to a surface onto which a foam was placed:
1. Place a thermometer in a clean glass vial and allow it to come to equilibrium.
2. Measure and record the temperature.
3. Release foam about 5 gm onto the thermometer.
4. Observe temperature for 300 sec.

The procedure was performed on regular; different cooling and heating foam formulations (per examples below).

Results: For all foams tested by the above method as seen in the examples hereinbelow, no detectable significant temperature difference was noted between the surface temperature, foam temperature and ambient initial temperature. This is indicative that the foams produced in the examples below did not exhibit a measurable exothermic or endothermic reaction. Thus, the foams tested should not induce a significant temperature effect at the target site primarily due to the cooling effect of the propellant. In certain embodiments, it may be possible for there to be an interaction between chemicals in the skin or other target site and the foam composition, particularly for the non-aqueous compositions. For example, by moisture in the skin being absorbed by hygroscopic pharmaceutical recipients, like glycols. Nevertheless, a main aim is to deliver a sensation via a foam vehicle, where the prime sensation is due to pharmaceutical stimulation rather than an actual physical effect. In one or more embodiments, the sensation may be a combination of pharmaceutical stimulation and physical effect. For example, where an excess of propellant may provide an initial physical cooling and the sensation agent provides a prolonged sensation, without further cooling. The vehicles disclosed herein are adapted to provide the main sensation with or without an initial physical cooling sensation.

Section A

Cooling

Example 1

Emollient Emulsion Foamable Composition with 10% Menthol Crystals and Avocado Oil a) Formulation

| Ingredient Name | Function | % w/w |
| --- | --- | --- |
| Avocado oil | emollient and solvent | 10 |
| PEG 40 Stearate | Stabilizing emulsifier | 2.31 |

-continued

| Stearyl Alcohol | Co-emulsifier and foam stabilizer | 0.77 |
| --- | --- | --- |
| Isopropyl myristate | emollient | 4.62 |
| Mineral Oil | Emollient | 4.62 |
| Hypromellose | Stabilizing polymers | 0.23 |
| Xanthan gum | Stabilizing polymers | 0.23 |
| Polysorbate 80 | Stabilizing emulsifier | 0.77 |
| GMS | Co-emulsifier foam stabilizer | 0.39 |
| Menthol | Cooling agent | 10 |
| Water | Solvent | to 100 |
| TOTAL | | 100 |
| Propane/butane/isobutane | | 8 |

| | |
| --- | --- |
| Foam quality | Excellent |
| Color | White |
| Odor | Menthol |
| Density [g/cm$^3$] | 0.045 |
| Shakability | Good |
| pH | 6.63 |
| Collapse time [seconds] | >300 | b) Emollient+avocado oil+10% menthol crystals: Mean cooling effect on three subjects over time is 12.7

| Time | Score |
| --- | --- |
| 0 | 2.00 |
| 5' | 1.33 |
| 15' | 2.33 |
| 30' | 2.00 |
| 60' | 2.00 |
| 120' | 1.33 |
| after washing | 1.67 |

Sum total of points for this formulation for all subjects is: 38 c) Emollient+avocado oil+10% menthol crystals: Foam satisfaction Parameters

| Ease of application | skin absorption | stickiness | odor | oily residue | foam stability | Shiny Look | overall satisfaction |
| --- | --- | --- | --- | --- | --- | --- | --- |
| 3.3 | 2.7 | 4.0 | 3.0 | 3.7 | 3.3 | 3.3 | 3.7 |

Sum total of points for this formulation for all subjects is: 107

Comments: Emollient emulsion foam provided a reasonable and prolonged cooling sensation; excellent foam quality; moisturizing; Comprises an oil phase, a water phase, a surfactant combination supported by co emulsifiers and a combination of polymeric agents. The co emulsifiers are non essential and can be omitted although some adjustment may be needed to the surfactant combination as will be appreciated by someone skilled in the art.

Note: The propellant can be added at a concentration of about 3% to about 25% or more.

Example 2

Emollient Emulsion Foamable Composition with 10% Menthol Crystals and Avocado Oil and 15% Ethanol a) Emollient+10% menthol crystals+15% ethanol: Formulation

| Ingredient Name | Function | % w/w |
| --- | --- | --- |
| Avocado oil | emollient and solvent | 10 |
| PEG 40 Stearate | Stabilizing emulsifier | 2.31 |

-continued

| | | |
|---|---|---|
| Stearyl Alcohol | Co-emulsifier and foam stabilizer | 0.77 |
| Isopropyl myristate | emollient | 4.62 |
| Mineral Oil | Emollient | 4.62 |
| hypromellose | Stabilizing polymers | 0.23 |
| xanthan gum | Stabilizing polymers | 0.23 |
| Polysorbate 80 | Stabilizing emulsifier | 0.77 |
| GMS | Co-emulsifier foam stabilizer | 0.39 |
| Menthol | Cooling agent | 10 |
| ETHANOL | Solvent - penetration enhancer | 15 |
| Water | Solvent | to 100 |
| TOTAL | | 100 |
| Propane/butane/isobutane | | 8 |

| | |
|---|---|
| Foam quality | Good |
| Color | White |
| Odor | Menthol |
| Density [g/cm³] | 0.044 |
| Shakability | Moderate |
| pH | 5.89 |
| Collapse time [seconds] | 300 | b) Emollient+avocado oil+10% menthol crystals+15% ethanol: Mean cooling effect on four subjects over time is 13.34

| Time | Score |
|---|---|
| 0 | 1.75 |
| 5' | 1.875 |
| 15' | 2.5 |
| 30' | 2.75 |
| 60' | 2.25 |
| 120' | 1.25 |
| after washing | 1 |

Sum total of points for this formulation for all subjects is: 53.5 c) Emollient+avocado oil+10% menthol crystals+15% ethanol: Foam satisfaction Parameters

| Ease of application | skin absorption | stickiness | odor | oily residue | foam stability | Shiny Look | overall satisfaction |
|---|---|---|---|---|---|---|---|
| 4.25 | 3.75 | 5 | 4 | 4.25 | 3.75 | 2 | 4 |

Sum total of points for this formulation for all subjects is: 124

Comments: Emollient foam provided reasonable and prolonged cooling sensation; good foam quality; moisturizing; Comprises an oil phase, water phase, surfactant combination supported by co emulsifiers and a combination of polymeric agents plus a polar solvent as a penetration enhancer. Menthol in the above formulation achieves good penetration on its own so the presence of 15% ethanol is of only marginal effect. Ethanol is not essential and may be omitted or replaced by other penetrating agents such as transcutol; DMI; and the like. See section on penetration agents.
Note: The propellant can be added at a concentration of about 3% to about 25% or more.

Example 3

Emollient Emulsion Foamable Composition with 15% Menthol Crystals a) Formulation

| Ingredient Name | Function | % w/w |
|---|---|---|
| Capric/caprilic triglyceride | Emollient and solvent | 6 |
| Stearic acid | Co-emulsifier and foam stabilizer | 2 |
| hypromellose | Stabilizing polymers | 0.3 |
| xanthan gum | Stabilizing polymers | 0.3 |
| Steareth-2 | Stabilizing emulsifier | 2.5 |
| Steareth-21 | Stabilizing emulsifier | 3 |
| Menthol | Cooling agent | 15 |
| Propylene Glycol | Solvent; moisturizer; penetration enhancer | 3 |
| Water | solvent | To 100 |
| TOTAL | | 100 |
| Propane/butane/isobutane | | 8 |

| | |
|---|---|
| Foam quality | Good |
| Color | White |
| Odor | Menthol |
| Density [g/cm³] | 0.025 |
| Shakability | Moderate |
| pH | 6.26 |
| Collapse time [seconds] | >300 | b) Emollient+15% menthol crystals: Mean cooling effect on four subjects over time is 13.88

| Time | Score |
|---|---|
| 0 | 1.375 |
| 5' | 2 |
| 15' | 3.25 |
| 30' | 3.5 |
| 60' | 2.5 |
| 120' | 1.25 |
| after washing | 1.25 |

Sum total of points for this formulation for all subjects is 60.5 c) Emollient+15% menthol crystals: Foam satisfaction Parameters

| Ease of application | skin absorption | stickiness | odor | oily residue | foam stability | Shiny Look | overall satisfaction |
|---|---|---|---|---|---|---|---|
| 4 | 4 | 3.5 | 3.75 | 3.5 | 4.5 | 2.75 | 3.75 |

Sum total of points for this formulation for all subjects is: 119

Comments: Emollient foam provided excellent and prolonged cooling sensation; good foam quality; moisturizing. Comprises an oil phase, a water phase, a surfactant combination supported by a co-emulsifier and a combination of polymeric agents. The propylene glycol is non essential.
Note: The propellant can be added at a concentration of about 3% to about 25% or more.

Example 4

Emollient Emulsion Foamable Composition with 15% Peppermint Oil a) Formulation

| CTFA Name | Function | % w/w |
|---|---|---|
| Capric/caprilic Triglyceride | Emollient and solvent | 6 |
| Stearic acid | Co-emulsifier and foam stabilizer | 2 |
| hypromellose | Stabilizing polymers | 0.3 |
| xanthan gum | Stabilizing polymers | 0.3 |
| Steareth-2 | Stabilizing emulsifier | 2.5 |
| Steareth-21 | Stabilizing emulsifier | 3 |
| PEPPERMINT OIL | Cooling agent | 15 |

-continued

| Ingredient | Function | |
|---|---|---|
| Propylene Glycol | Solvent/moisturizer/penetration enhancer | 3 |
| Permulen | | 0.1 |
| TEA | | To pH 7 |
| Water | solvent | To 100 |
| TOTAL | | 100 |
| Propane/butane/isobutane | | 8 |

| | | |
|---|---|---|
| Foam quality | Good | |
| Color | White | |
| Odor | Menthol | |
| Density [g/cm³] | 0.028 | |
| Shakability | Low | |
| pH | 6.17 | |
| Collapse time [seconds] | >300 | | b) Emollient+15% peppermint oil: Mean cooling effect on four subjects over time is 11.75

| Time | Score |
|---|---|
| 0 | 1.75 |
| 5' | 1.5 |
| 15' | 2.25 |
| 30' | 2.5 |
| 60' | 1.75 |
| 120' | 1 |
| after washing | 1 |

Sum total of points for this formulation for all subjects is: 47 c) Emollient+15% peppermint oil Foam satisfaction Parameters

| Ease of application | skin absorption | stickiness | odor | oily residue | foam stability | Shiny Look | overall satisfaction |
|---|---|---|---|---|---|---|---|
| 4 | 3.75 | 4 | 3.25 | 3.75 | 4.5 | 3.25 | 3.75 |

Sum total of points for this formulation for all subjects is: 121

Comments: Emollient foam provided reasonable and prolonged cooling sensation; good foam quality; moisturizing; Comprises an oil phase, a water phase, a surfactant combination supported by a co-emulsifier and a combination of polymeric agents. The propylene glycol is non-essential. The peppermint oil reduces the viscosity of the emulsion and is matrix destabilizing.
Note: The propellant can be added at a concentration of about 3% to about 25% or more.

Example 5

Emollient Emulsion Foamable Composition with 15% Menthol Crystals and 25% propellant a) Formulation

| Ingredient name | Function | % w/w |
|---|---|---|
| Stearic acid* | Co-emulsifier and foam stabilizer | 3 |
| Steareth-2* | Stabilizing emulsifier | 2 |
| Steareth-21* | Stabilizing emulsifier | 3 |
| Methylcellulose* | Co-emulsifier and foam stabilizer | 0.3 |
| Xanthan gum* | Co-emulsifier and foam stabilizer | 0.3 |
| Menthol crystal | Cooling agent | 15 |
| Water* | Solvent | To 100 |
| Glyceryl monostearete | Co-emulsifier foam stabilizer | 2 |

-continued

| Ingredient name | Function | % w/w |
|---|---|---|
| Propellant (Propane/Butane/Isobutane) | | 25 | b) Emollient+25% propellant+Menthol crystals: Mean cooling effect on four subjects over time

| Time | Score |
|---|---|
| 0 | 1.7 |
| 5' | 1.0 |
| 15' | 2.3 |
| 30' | 2.7 |
| 60' | 1.7 |
| 120' | 1.3 |
| after washing | 1.0 |

Sum total of points for this formulation for all subjects is: 37 c) Emollient+25% propellant+Menthol crystals: Foam satisfaction Parameters

| Ease of application | skin absorption | stickiness | odor | oily residue | foam stability | Shiny Look | overall satisfaction |
|---|---|---|---|---|---|---|---|
| 4.0 | 3.3 | 3.0 | 3.0 | 3.0 | 3.0 | 4.0 | 3.7 |

Sum total of points for this formulation for all subjects is: 76

Comments: Emollient foam provided good cooling sensation; good foam quality; doesn't require preservative.
Note: The propellant can be added at a concentration of about 3% to about 25% or more.

Example 6

Waterless Foamable Composition With 15% Menthol Crystals (Formula Number—28)

a) Formulation

| Ingredient Name | Function | % w/w |
|---|---|---|
| PEG 4000 | Firming wax | 7.5 |
| Stearic acid | Co-emulsifier and foam stabilizer | 2 |
| Hydroxupropyl cellulose | Stabilizing polymers | 2 |
| Steareth-2 | Stabilizing emulsifier | 2.5 |
| Steareth-21 | Stabilizing emulsifier | 3 |
| Menthol | Cooling agent | 15 |
| Propylene Glycol | Solvent/moisturizer/penetration enhancer | 68 |
| TOTAL | | 100 |
| Propane/butane/isobutane | | 8 |

| | |
|---|---|
| Foam quality | Fairly good |
| Color | White |
| Odor | Menthol | b) Mean cooling effect on four subjects over time

| Time | Score |
|---|---|
| 0 | 1 |
| 5' | 1.125 |
| 15' | 1.375 |
| 30' | 2 |

-continued

| Time | Score |
|---|---|
| 60' | 2.5 |
| 120' | 1.5 |
| after washing | 1 |

Sum total of points for this formulation for all subjects is: 42 c) Foam satisfaction Parameters

| Ease of appli-cation | skin ab-sorption | stickiness | odor | oily residue | foam stability | Shiny Look | overall satis-faction |
|---|---|---|---|---|---|---|---|
| 4 | 2.5 | 3.25 | 3.75 | 2 | 1 | 1.75 | 2.25 |

Sum total of points for this formulation for all subjects is: 82

Comments: Waterless foam provided reasonable and prolonged cooling sensation with a delayed onset; fairly good foam quality; moisturizing; doesn't require preservative. Any high molecular weight PEG (for example 1500, 2000, 4000, 6000 or 8000) or combinations of high molecular weight PEG with lower molecular weight PEG (for example 200, 400, 600) may be used.

Note: The propellant can be added at a concentration of about 3% to about 25% or more.

Example 7

Waterless Foamable Composition With 10% Peppermint Oil (Formula Number—32)

a) Formulation

| Ingredient Name | Function | % w/w |
|---|---|---|
| PEG 4000 | Firming wax | 7.5 |
| Stearic acid | Co-emulsifier and foam stabilizer | 2 |
| Hydroxypropyl cellulose | Stabilizing polymers | 2 |
| Steareth-2 | Stabilizing emulsifier | 2.5 |
| Steareth-21 | Stabilizing emulsifier | 3 |
| PEPPERMINT OIL | Cooling agent | 10 |
| Propylene Glycol | Solvent/moisturizer - penetration enhancer | 73 |
| TOTAL |  | 100 |
| Propane/butane/isobutane |  | 8 |

| Foam quality | Fairy good |
|---|---|
| Color | White |
| Odor | Menthol |
| Cooling score (Σ of total points for this formulation from all people) | 36 | a) Mean cooling effect on Four subjects over time is 9

| Time | Score |
|---|---|
| 0 | 1 |
| 5' | 1 |
| 15' | 1.75 |
| 30' | 2 |
| 60' | 1.25 |
| 120' | 1 |
| after washing | 1 |

Sum total of points for this formulation for all subjects is: 36 c) Foam satisfaction Parameters

| Ease of appli-cation | skin ab-sorption | stickiness | odor | oily residue | foam stability | Shiny Look | overall satis-faction |
|---|---|---|---|---|---|---|---|
| 4 | 3 | 3.25 | 3.5 | 2.25 | 3.5 | 2.5 | 3 |

Sum total of points for this formulation for all subjects is: 100

Comments: Waterless foam provided reasonable and medium term cooling sensation with delayed onset; fairly good foam quality; moisturizing; doesn't require preservative. Any high molecular weight PEG (for example 1500, 2000, 4000, 6000 or 8000) or combinations of high molecular weight PEG with lower molecular weight PEG (for example 200, 400, 600) may be used. The peppermint oil has a thinning effect on the composition, which is to some extent counterbalanced or ameliorated by the high molecular weight PEG.

Note: The propellant can be added at a concentration of about 3% to about 25% or more.

Relaxing or Soothing

Example 8

Emollient Emulsion Foamable Relaxing or Soothing Composition With Hamamelis

|  | % w/w |
|---|---|
| Mineral oil | 6.00 |
| Isopropyl myristate | 6.00 |
| Glyceryl monostearate | 0.50 |
| Stearyl alcohol | 1.00 |
| Xanthan gum | 0.30 |
| Methocel K100M | 0.30 |
| Polysorbate 80 | 1.00 |
| PEG-40 stearate | 3.00 |
| *Hamamelis* glycerin fluid extract (Alban Muller, France) | 10.00 |
| EDTA disodium | 0.20 |
| Phenonip | 0.30 |
| Water pure | to 100 |
| Propellant (propane and butane 20:80) | 8.0 |

| Foam quality | Excellent |
|---|---|
| Density [g/cm$^3$] | 0.04 |
| Collapse time | >120 |
| Shakability | Yes |
| Odor | slight |

Comments: Emollient foam capable of providing a soothing sensation; excellent foam quality; moisturizing. It comprises an oil phase, water phase, a surfactant combination supported by co emulsifiers and a combination of polymeric agents, plus a preservative and a chelating agent. The chelating agent is non essential. The co emulsifiers are non essential and can be omitted although some adjustment may be needed to the surfactant combination as will be appreciated by someone skilled in the art.

Note: The propellant can be added at a concentration of about 3% to about 25% or more.

Warming

Example 9

Prophetic Emollient Emulsion Foamable Warming Composition With Capsaicin and Mineral Oil

| Ingredient name | % w/w |
| --- | --- |
| Mineral oil | 4.62 |
| Isopropyl myristate | 4.62 |
| Glyceryl monostearate | 0.39 |
| Polysorbate 80 | 0.77 |
| PEG-40 stearate | 2.31 |
| Stearyl alcohol | 0.77 |
| Hydroxypropyl methylcellulose | 0.23 |
| Xanthan | 0.23 |
| Water | TO 100 |
| Capsaicin | 0.025 |
| Total: | 100.00 |
| Propellant (Propane/Butane/Isobutane) | 8 |

Example 10

Prophetic Waterless Foamable Warming Composition With Capsaicin

| Ingredient name | % w/w |
| --- | --- |
| PEG 4000 | 7.5 |
| Capsaicin | 0.025 |
| Hydroxypropyl cellulose | 2 |
| Stearic acid | 2 |
| Steareth-2 | 2.5 |
| Steareth-21 | 3 |
| Propylene glycol | To 100 |
| Propellant (Propane/Butane/Isobutane) | 8 |

Example 11

Prophetic Emollient Emulsion Foamable Warming Composition With Capsaicin and MCT

| Ingredient name | % w/w |
| --- | --- |
| MCT | 6 |
| Stearic acid | 2 |
| Steareth 2 | 2.5 |
| Steareth-21 | 3 |
| Capsaicin | 0.025 |
| Propylene Glycol | 3 |
| Xanthan gum | 0.3 |
| Hypromellose | 0.3 |
| Water | To 100 |
| Propellant (Propane/Butane/Isobutane) | 8 |

Comments:

It is possible to use any of the above exemplary warming formulations with other warming agents, for example, methyl salicylate. Apart from its warming effect methyl salicylate is an analgesic and counter irritant. Lists of applicable warming agents are described in the specification. An effective amount of the warming agent is introduced into the formulation in place of capsaicin and the amount of the main carrier is adjusted to bring the formulation to 100%, which in the case of the waterless composition is propylene glycol and in the case of the emollient emulsion composition is water. The amount of methyl salicylate is of the order of 5 to 10%.

It is also possible to use combinations of warming agents. The combination of capsaicin with methyl salicylate, for example, may be useful. Methyl salicylate has a quick onset whilst capsaicin does not so a combination may be helpful in cases where pain relief is sought.

It is also possible to modulate, potentate, increase, reduce, or ameliorate the warming effect by introducing into the composition a sensation modifying agent. I an embodiment the warming effect or sensation maybe reduced by addition of a cooling agent in the composition.

The formulations may contain polar solvents, which contribute to skin penetration of an active agent Foam With Additional Therapeutic Agents

Example 12

Foamable Oil in Water Emulsion Foamable Compositions, Containing Menthol as Cooling Agent and Coal Tar Extract and Salicylic Acid as Additional Therapeutic Agents

| Ingredient name | CTR005 % W/W | CTR006 % W/W |
| --- | --- | --- |
| Menthol (Sensation modifying agent) | 1 | 1 |
| Coal tar extract (Additional therapeutic agent) | 10 | 10 |
| Salicylic acid (Additional therapeutic agent) | — | 5 |
| Hydrocortisone (Additional therapeutic agent) | 1 | — |
| PPG-15 Stearyl ether | — | 3 |
| Isopropyl Myristate | 10 | 5 |
| Octyldodecanol | 12 | 12 |
| Stearyl Alcohol | 2 | 1 |
| Glycerin | — | 3 |
| Lanolin | — | 2 |
| Laureth-4 | — | 2 |
| Emulgin B2 | — | 1.5 |
| Glyceryl Stearate | 1.5 | — |
| PEG-40 Stearate | 3 | — |
| CMC | — | 0.5 |
| Methocel K100M | 0.28 | — |
| Xanthan gum | 0.28 | — |
| Propylene Glycol | — | 5 |
| Polysorbate 60 | 1 | — |
| Water, purified | To 100 | To 100 |
| Propellant | 8 | 8 |

Comments: The above formulations provided excellent moisturizing emollient foams with improved sensation by ameliorating the negative sensation effect of coal tar.

Section B

Cooling

Example 13

A) Waterless propylene glycol formulation containing peppermint oil as cooling agent

| | SMTC004-071205 |
|---|---|
| Steareth 2 | 2.00 |
| polysorbate 80 | 2.00 |
| Glyceryl monostearate | 2.00 |
| Hydroxypropyl cellulose | 1.00 |
| peppermint oil | 10.00 |
| Propylene Glycol | 83.00 |
| Total: | 100.00 |
| Propellant (AP-70) | 8.00 |
| Results PFF | |
| Viscosity | 148.97 |
| Centrifgation 1K | stable |
| Centrifgation 3K | stable |
| FOAM | |
| Quality | G-E |
| Color | White |
| Collapse time (sec.) | 95/F |
| Density (gr/ml) | 0.070 |
| Bubble size (μm) | 180 |
| Bubble size (%-above 500 μm) | 6.30 |
| temperature change | T-0 MINUTES = 13° C. T-5 MINUTES = 12° C. |

*G-E = Good to Excellent

Comments: This waterless single phase formulation provides a stable vehicle for peppermint oil that can generate good quality foam and which can withstand 3000 rpm. The surfactants and a polymeric agent provide viscosity support and aid foaming. On forming foam there is no significant temperature change when measured on a glass surface. When the formulation is applied to the skin, however, the peppermint oil provides a sensation of cooling, which may be potentiated by the evaporation of propellant and the lower temperature of the foam compared to the skin.

B) A waterless PG formulation and two oil in water emulsion formulations containing menthol crystals as cooling agent

| | SMTC005-071205 | SMTC006-071205 cf example 3 | SMTC007-071211 cf example 12 |
|---|---|---|---|
| MCT | | 6.00 | |
| Isopropyl myristate | | | 10.00 |
| Octyldodecanol | | | 10.00 |
| Stearic acid | | 2.00 | |
| Stearyl alcohol | | | 2.00 |
| Cetostearyl alcohol | 2.00 | | |
| Steareth 2 | 2.00 | 4.20 | |
| Steareth-21 | | 1.40 | |
| polysorbate 80 | 2.00 | | |
| Glyceryl monostearate | 2.00 | | 1.40 |
| PEG-40 stearate | | | 3.10 |
| Polysorbate 60 | | | 1.20 |
| Xanthan gum | | 0.30 | 0.28 |
| Methocell k100M | | 0.30 | 0.28 |
| Hydroxypropyl cellulose | 1.00 | | |
| Water | | 67.80 | 59.74 |
| menthol crystals | 10.00 | 15.00 | 1.00 |
| Propylene Glycol | 81.00 | 3.00 | |
| Coal tar | | | 10.00 |
| Hydrocortisone butyrate | | | 1.00 |
| Total: | 100.00 | 100.00 | 100.00 |
| Propellant (AP-70) | 8.00 | 8.00 | 8.00 |

| | SMTC005-071205 | SMTC006-071205 cf example 3 | SMTC007-071211 cf example 12 |
|---|---|---|---|
| Results PFF | | | |
| Viscosity | 4447.05 | 4527.04 | 2037.57 |
| Centrifgation 1K | stable | Stable | stable |
| Centrifgation 3K | stable | Stable | stable |
| FOAM | | | |
| Quality | G-E | G-E | G-E |
| Color | White | White | Slightly Yellow |
| Collapse time (sec.) | >300/G | >300/FG | >300/FG |
| Density (gr/ml) | 0.060 | 0.043 | 0.039 |
| Bubble size (μm) | 62 | 99 | 112 |
| Bubble size (%-above 500 μm) | 0.00 | 0.00 | 0.00 |

Comments: Formulation 5 is a single phase composition that provides a stable vehicle for menthol crystals that can generate good quality foam capable of withstanding 3000 rpm and having a collapse time in excess of 5 minutes. The surfactants, adjuvant and a polymeric agent provide viscosity support and aid foaming. The other two formulations 6 and 7 are stable oil in water emulsions that can generate good quality foam, are resistant to centrifugation at 3000 rpm and have a collapse time in excess of 5 minutes. All the formulations can accommodate substantial amounts of cooling sensation agent. In an embodiment the cooling agent is a combination of at least two cooling agents. In a further embodiment the cooling agent may be used in combination with a soothing agent. The coal tar formulation is yellow prior to addition of the propellant but upon discharge from the canister and release as a foam the color is dissipated such that the foam is only slightly yellow, which may be an advantage for its use.

Warming

Example 14

A Waterless PG Formulation and Two Oil in Water Emulsion Formulations Containing Capsaicin as Warming Agent

| | SMTC001-071204 cf example 11 | SMTC002-071204 cf example 9 | SMTC003-071204 |
|---|---|---|---|
| MCT | 8.00 | | |
| Mineral oil | | 5.00 | |
| Isopropyl myristate | | 5.00 | |
| Stearic acid | 2.00 | | |
| Stearyl alcohol | | 1.00 | |
| Cetostearyl alcohol | | | |
| Steareth 2 | 6.70 | | 2.00 |
| Steareth-21 | 1.80 | | |
| Glyceryl monostearate | | 1.80 | |
| PEG-40 stearate | | 1.50 | |
| Xanthan gum | 0.30 | 0.23 | |
| Methocell k100M | 0.30 | 0.23 | |
| Water | 77.87 | 82.21 | |
| Capsaicin | 0.03 | 0.03 | 0.03 |
| Propylene Glycol | 3.00 | 3.00 | 97.97 |
| Total: | 100.00 | 100.00 | 100.00 |
| Propellant (AP-70) | 8.00 | 8.00 | 8.00 |

-continued

|  | SMTC001-071204 cf example 11 | SMTC002-071204 cf example 9 | SMTC003-071204 |
|---|---|---|---|
| Results PFF |  |  |  |
| Viscosity | 18636.03 | 1085.77 | 4367.07 |
| Centrifgation 1K | stable | Stable | stable |
| Centrifgation 3K | stable | Stable | stable |
| FOAM |  |  |  |
| Quality | G-E | G-E | G-E |
| Color | White | White | White |
| Collapse time (sec.) | >300/FG | >300/FG | >300/G |
| Density (gr/ml) | 0.078 | 0.036 | 0.048 |
| Bubble size (μm) | 78 | 96 | 85 |
| Bubble size (%-above 500 μm) | 0.00 | 0.00 | 0.00 |
| temperature change | T-0 MINUTES = 13 C. T-5 MINUTES = 14 C. |  |  |

Comments: Formulation 3 is a waterless single phase composition that provides a stable vehicle for capsaicin that can generate good quality foam capable of withstanding 3000 rpm and having a collapse time in excess of 5 minutes. The surfactants, adjuvant and a polymeric agent provide viscosity support and aid foaming. The other two formulations 1 and 2 are stable oil in water emulsions that can generate good quality foam, are resistant to centrifugation at 3000 rpm and have a collapse time in excess of 5 minutes. On forming foam there is no significant temperature change when measured on a glass surface. When the formulation is applied to the skin, however, the capsaicin should provide a sensation of warming.

In an embodiment the warming agent is a combination of at least two warming agents. In a further embodiment the warming agent may be used in combination with a soothing agent.

Soothing

Example 15

A) Two oil in water stable emulsion formulations containing ginger oil as soothing agent

|  | SMTC010-071218 | SMTC011-071223 |
|---|---|---|
| Cetostearyl alcohol |  | 2.00 |
| Steareth 2 |  | 1.40 |
| Steareth-21 |  | 4.50 |
| polysorbate 80 | 1.40 |  |
| Glyceryl monostearate | 1.30 |  |
| PEG-40 stearate | 1.80 |  |
| Xanthan gum | 0.30 | 0.30 |
| Methocell k100M | 0.30 | 0.30 |
| Avicel RC581 |  |  |
| Water | 84.90 | 81.50 |
| ginger oil | 10.00 | 10.00 |
| Total: | 100.00 | 100.00 |
| Propellant (AP-70) | 8.00 | 8.00 |
| Results PFF |  |  |
| Viscosity | 4399.06 | 1150.75 |
| Centrifgation 1K | stable | stable |
| Centrifgation 3K | stable | stable |

|  | SMTC010-071218 | SMTC011-071223 |
|---|---|---|
| FOAM |  |  |
| Quality | FG | G-E |
| Color | slight yellow | Off-white |
| Collapse time (sec.) | 30/F | >300/G |
| Density (gr/ml) |  | 0.034 |
| Bubble size (μm) |  | 105 |
| Bubble size (%-above 500 μm) |  | 0.00 |
| temperature change |  | T-0 MINUTES = 13 C. T-5 MINUTES = 13 C. |

Comments: By altering the surfactant mix a good quality foam was generated that is resistant to centrifugation and has a collapse time in excess of 5 minutes. The vehicle is capable of supporting substantial amounts of ginger oil. On forming foam there is no significant temperature change when measured on a glass surface. When the formulation is applied to the skin, however, the ginger oil should provide a sensation of soothing.

B) Gel formulation containing aloe vera as soothing agent

|  | SMTC012-071225 | SMTC013-071225 |
|---|---|---|
| polysorbate 80 | 2.00 | 4.00 |
| Avicel RC581 | 2.00 | 4.00 |
| Water | 94.00 | 65.00 |
| Aloe vera | 2.00 | 2.00 |
| Diethylene glycol monoethyl ether |  | 25.00 |
| Total: | 100.00 | 100.00 |
| Propellant (AP-70) | 8.00 |  |
| Results PFF |  |  |
| Viscosity | 39.99 | 2273.51 |
| Centrifgation 1K | not stable | not stable |
| Centrifgation 3K | not stable | not stable |
| FOAM |  |  |
| Quality | G-E | G-E |
| Color | White | White |
| Collapse time (sec.) | 95/F | 140/F |
| Density (gr/ml) | 0.044 | 0.034 |
| Bubble size (μm) | 131 | 113 |
| Bubble size (%-above 500 μm) | 0.00 | 0.00 |

Comments: These water gel formulations are single phase compositions that provide a vehicle for aloe vera that can generate good quality foam having a collapse time in excess of 1.5 minutes. When the formulation is applied to the skin, the aloe vera should provide a sensation of soothing. In an embodiment the soothing agent is a combination of at least two soothing agents. In a further embodiment the soothing agent may be used in combination with a cooling agent or with a warming agent.

C) Emollient emulsion formulation containing aloe vera as soothing agent

|  | SMTC014-080103 |
|---|---|
| Mineral oil | 11.00 |
| Cetostearyl alcohol | 2.00 |
| Steareth 2 | 4.30 |
| Steareth-21 | 2.90 |
| Xanthan gum | 0.30 |

-continued

|  | SMTC014-080103 |
| --- | --- |
| Methocell k100M | 0.30 |
| Water | 77.20 |
| Aloe vera | 2.00 |
| Total: | 100.00 |
| Propellant (AP-70) | 8.00 |
| Results |  |
| PFF |  |
| Viscosity | 18300.10 |
| Centrifgation 1K | stable |
| Centrifgation 3K | Stable |
| FOAM |  |
| Quality | G-E |
| Color | White |
| Odor | Characteris. odor |
| Collapse time (sec.) | >300/G |
| Density (gr/ml) | 0.070 |
| Bubble size (μm) | 48 |
| Bubble size (%-above 500 μm) | 0.00 |

Comments: These emollient emulsion formulations provide a vehicle for aloe vera that can generate good quality foam having a collapse time in excess of 5 minutes and is stable to centrifugation. When the formulation is applied to the skin, the aloe vera should provide a sensation of soothing. In an embodiment the soothing agent is a combination of at least two soothing agents. In a further embodiment the soothing agent may be used in combination with a cooling agent or with a warming agent.

The references cited herein teach many principles that are applicable to the present invention. Therefore the full contents of these publications are incorporated by reference herein where appropriate for teachings of additional or alternative details, features and/or technical background.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art.

The invention claimed is:

1. A topical composition, comprising a foamable base composition and a hydrocarbon propellant,
   wherein the foamable base composition is an oil in water emulsion comprising:
   i. about 6% to about 22% by weight of the foamable base composition of a hydrophobic solvent comprising a non-volatile hydrophobic solvent selected from the group consisting of at least two of isopropyl myristate, a triglyceride and a silicone oil;
   ii. about 0.5% to about 3% by weight of the foamable base composition of a sensation or sensation modifying agent;
   iii. a coal tar;
   iv. about 0.1% to about 5% by weight of the foamable base composition of a polymeric agent, wherein the polymeric agent is selected from the group consisting of a locust bean gum, sodium alginate, sodium caseinate, an egg albumin, a gelatin agar, a carrageenan gum, a xanthan gum, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinylpyrrolidone, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, methylhydroxyethylcellulose, a hydroxyethyl carboxymethylcellulose, a carboxymethyl cellulose, a cationic cellulose, PEG 1000, PEG 4000, PEG 6000, PEG 8000, a sodium carboxymethyl cellulose, a microcrystalline cellulose, a polyacrylate and mixtures of any two or more thereof; and
   v. about 40% to about 90% by weight of the foamable base composition of water;
   wherein the hydrocarbon propellant is selected from the group consisting of butane, propane, isobutane, isobutene and mixtures of any two or more thereof;
   wherein the weight ratio of the foamable base composition to the hydrocarbon propellant ranges from about 100:3 to about 100:25;
   wherein the topical composition is stored in a pressurized container and upon release expands to form a non-crackling short term stable foam that breaks under mechanical force;
   wherein the foam produces at least one prolonged sensation at a delivery site upon dispensing from an aerosol container for a period of at least about 5 minutes; and
   wherein the prolonged sensation is not primarily due to the propellant or an exothermic reaction.

2. The composition of claim 1, wherein the foam neutralizes, ameliorates or hides one or more undesired properties or negative sensation effect of said coal tar extract.

3. The composition of claim 1, wherein the hydrocarbon propellant is a mixture of propane, butane, and isobutane.

4. The composition of claim 1, wherein the sensation or sensation modifying agent is selected from the group consisting of menthol, an isomer of menthol, a menthol derivative, 4-Methyl-3-(1-pyrrolidinyl)-2[5H]-furanone, WS-23, icilin, icilin unilever analog, 5-methyl-4-(1-pyrrolidinyl)-3-[2H]-furanone, 4,5-dimethyl-3-(1-pyrrolidinyl)-2[5H]-furanone, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate, menthyl succinate alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, spearmint oil, and mixtures of any two or more thereof.

5. The composition of claim 1, wherein the short term stable foam is stable at the delivery site for at least one minute.

6. The composition of claim 1, wherein the coal tar is provided as a coal tar extract or tincture.

7. The composition of claim 1, wherein the hydrophobic solvent of the oil in water emulsion is present at a concentration of at least about 10% by weight of the foamable composition.

8. The composition of claim 1, wherein the hydrophobic solvent of the oil in water emulsion comprises isopropyl myristate.

9. The composition of claim 1, wherein the hydrophobic solvent of the oil in water emulsion comprises a silicone oil.

10. The composition of claim 9, wherein the silicone oil is selected from the group consisting of a dimethicone, a polyalkyl siloxane, a polyaryl siloxane, a polyalkylaryl siloxane, a polyether siloxane copolymer, a poly(dimethylsiloxane)-(diphenyl-siloxane) copolymer and mixtures of any two or more thereof.

11. The composition of claim 1, wherein the hydrophobic solvent of the oil in water emulsion comprises a triglyceride.

12. The composition of claim 6, wherein the foamable base composition comprises:
   a) from about 0.5% to about 4% by weight of the foamable base composition of at least one polymeric agent;
   b) from about 2.0% to about 8.5% by weight of the foamable base composition of a surfactant;
   c) from about 3% to about 25% by weight of the foamable base composition of a polar solvent;
   d) from 0% to about 2% by weight of the foamable base composition of a foam adjuvant; and
   e) from about 49% to about 88.5% by weight of the foamable base composition of water; and
   wherein the polar solvent range includes polar solvent present in the coal tar extract.

13. The composition of claim 12, wherein the sensation modifying agent is a cooling agent comprising menthol, an isomer of menthol, a menthol derivative, 4-Methyl-3-(1-pyrrolidinyl)-2[5H]-furanone, WS-23, icilin, icilin unilever analog, 5-methyl-4-(1-pyrrolidinyl)-3-[2H]-furanone, 4,5-dimethyl-3-(1-pyrrolidinyl)-2[5H]-furanone, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate, menthyl succinate alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, spearmint oil and mixtures of any two or more thereof.

14. The composition of claim 12, wherein the hydrophobic solvent further comprises a solvent selected from the group consisting of an essential oil, octyl dodecanol, lanolin, and mixtures of any two or more thereof.

15. The composition of claim 12, wherein the polar solvent is selected from the group consisting of a short chain alcohol, glycerol, propylene glycol and mixtures of any two or more thereof.

16. The composition of claim 15, wherein the short chain alcohol is ethanol.

17. The composition of claim 12, wherein the surfactant is selected from the group consisting of ceteareth 20, glyceryl stearate, PEG 40 stearate, polysorbate 60, laureth-4 and mixtures of any two or more thereof.

18. The composition of claim 12, wherein the foam adjuvant is selected from the group consisting of a fatty alcohol having 15 or more carbons in the carbon chain, a fatty acid having 16 or more carbons in the carbon chain and mixtures of any two or more thereof.

19. The composition of claim 12, wherein the polymeric agent is selected from the group consisting of a hypromellose, a xanthan gum, a carboxymethylcellulose and mixtures of any two or more thereof.

20. The composition of claim 12,
   wherein the polymeric agent comprises a hypromellose or a xanthan gum; and
   wherein the polar solvent comprises a short chain alcohol and glycerin.

21. A method of treating or alleviating a disorder selected from the group consisting of hyperkeratinization, eczema, dandruff, seborrheic dermatitis, psoriasis, atopic dermatitis, and dermatitis, comprising administering topically to a delivery site having the disorder, a foam produced from a composition comprising a foamable base composition and a hydrocarbon propellant,
   i. about 6% to about 22% by weight of the foamable base composition of a hydrophobic solvent comprising a non-volatile hydrophobic solvent selected from the group consisting of at least two of isopropyl myristate, a triglyceride and a silicone oil;
   ii. about 0.5% to about 3% by weight of the foamable base composition of a sensation or sensation modifying agent;
   iii. a coal tar;
   iv. about 0.1% to about 5% by weight of the foamable base composition of a polymeric agent, wherein the polymeric agent is selected from the group consisting of a locust bean gum, sodium alginate, sodium caseinate, an egg albumin, a gelatin agar, a carrageenan gum, a xanthan gum, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinylpyrrolidone, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, methylhydroxyethylcellulose, a hydroxyethyl carboxymethylcellulose, a carboxymethyl cellulose, a cationic cellulose, PEG 1000, PEG 4000, PEG 6000, PEG 8000, a sodium carboxymethyl cellulose, a microcrystalline cellulose, a polyacrylate and mixtures of any two or more thereof; and
   v. about 40% to about 90% by weight of the foamable base composition of water;
   wherein the hydrocarbon propellant is selected from the group consisting of butane, propane, isobutane, isobutene and mixtures of any two or more thereof;
   wherein the weight ratio of the foamable base composition to the hydrocarbon propellant ranges from about 100:3 to about 100:25;
   wherein the topical composition is stored in a pressurized container and upon release expands to form a non-crackling short term stable foam that breaks under mechanical force;
   wherein the foam produces at least one prolonged sensation at a delivery site upon dispensing from an aerosol container for a period of at least about 5 minutes; and
   wherein the prolonged sensation is not primarily due to the propellant or an exothermic reaction.

22. The method of claim 21, wherein the hydrocarbon propellant comprises propane, butane, and isobutane.

23. The method of claim 21, wherein the sensation or sensation modifying agent is selected from the group consisting of menthol, an isomer of menthol, a menthol derivative, 4-Methyl-3-(1-pyrrolidinyl)-2[5H]-furanone, WS-23, icilin, icilin unilever analog, 5-methyl-4-(1-pyrrolidinyl)-3-[2H]-furanone, 4,5-dimethyl-3-(1-pyrrolidinyl)-2[5H]-furanone, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate, menthyl succinate alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, spearmint oil and mixtures of any two or more thereof.

24. The method of claim 21, wherein the short term stable foam is stable at the delivery site for at least one minute.

25. The method of claim 21, wherein the coal tar is provided as a coal tar extract or tincture.

26. The method of claim 21, wherein the hydrophobic solvent of the oil in water emulsion is present at a concentration of at least about 10% by weight of the foamable base composition.

27. The method of claim 21, wherein the hydrophobic solvent of the oil in water emulsion comprises isopropyl myristate.

28. The method of claim 21, wherein the hydrophobic solvent of the oil in water emulsion comprises a silicone oil.

29. The method of claim 28, wherein the silicone oil is selected from the group consisting of a dimethicone, a polyalkyl siloxane, a polyaryl siloxane, a polyalkylaryl siloxane, a polyether siloxane copolymer, a poly(dimethylsiloxane)-(diphenyl-siloxane) copolymer and mixtures of any two or more thereof.

30. The method of claim 21, wherein the hydrophobic solvent of the oil in water emulsion comprises a triglyceride.

31. The method of claim 25, wherein the foamable base composition comprises:
    a) from about 0.5% to about 4% by weight of foamable base composition of at least one polymeric agent;
    b) from about 2% to about 8.5% by weight of foamable base composition of a surfactant;
    c) from about 3% to about 25% by weight of foamable base composition of a polar solvent;
    d) from about 0% to about 2% by weight of foamable base composition of a foam adjuvant; and
    e) from about 49% to about 88.5% by weight of foamable base composition of water;
    wherein the polar solvent range includes polar solvent present in the coal tar extract.

32. The method of claim 31, wherein the sensation modifying agent is a cooling agent comprising menthol, an isomer of menthol, a menthol derivative, 4-Methyl-3-(1-pyrrolidinyl)-2[5H]-furanone, WS-23, icilin, icilin unilever analog, 5-methyl-4-(1-pyrrolidinyl)-3-[2H]-furanone, 4,5-dimethyl-3-(1-pyrrolidinyl)-2[5H]-furanone, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate, menthyl succinate alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, spearmint oil and mixtures of any two or more thereof.

33. The method of claim 31, wherein the hydrophobic solvent further comprises a solvent selected from the group consisting of an essential oil, octyl dodecanol, a lanolin or any and mixtures of any two or more thereof.

34. The method of claim 31, wherein the polar solvent is selected from the group consisting of a short chain alcohol, glycerol, propylene glycol and mixtures of any two or more thereof.

35. The method of claim 34, wherein the short chain alcohol is ethanol.

36. The method of claim 31, wherein the surfactant is selected from the group consisting of ceteareth 20, glyceryl stearate, PEG 40 stearate, polysorbate 60, laureth-4, and mixtures of any two or more thereof.

37. The method of claim 31, wherein the foam adjuvant is selected from the group consisting of a fatty alcohol having 15 or more carbons in the carbon chain, a fatty acid having 16 or more carbons in the carbon chain and mixtures of any two or more thereof.

38. The method of claim 31, wherein the polymeric agent is selected from the group consisting of hypromellose, xanthan gum, carboxymethylcellulose and mixtures of any two or more thereof.

39. The method of claim 31,
    wherein the polymeric agent comprises hypromellose or xanthan gum; and
    wherein the polar solvent comprises a short chain alcohol and glycerin.

40. A composition according to claim 1, wherein said foamable base composition further comprises a cyclomethicone.

41. A method according to claim 21, wherein said foamable base composition further comprises a cyclomethicone.

42. The composition of claim 1, further comprising a foam adjuvant.

43. The composition of claim 6, wherein the extract or tincture is about 2% to about 20% by weight of the foamable composition.

44. The composition of claim 25, wherein the extract or tincture is about 2% to about 20% by weight of the foamable composition.

* * * * *